US005750331A

United States Patent [19]

Miyamura et al.

[11] Patent Number: 5,750,331

[45] Date of Patent: May 12, 1998

[54] DIAGNOSTIC REAGENT FOR HEPATITIS C

[75] Inventors: Tatsuo Miyamura; Izumu Saito; Shizuko Harada, all of Tokyo-to; Yoshikazu Honda, Kamakura, all of Japan

[73] Assignee: Japan as represented by Director General of Agency of National Institute of Health, Tokyo-to, Japan

[21] Appl. No.: 325,630

[22] Filed: Oct. 19, 1994

Related U.S. Application Data

[63] Continuation of Ser. No. 956,993, Oct. 6, 1992, abandoned.

[30] Foreign Application Priority Data

Oct. 8, 1991 [JP] Japan .................................. 3-260824

[51] Int. Cl.$^6$ .................................................. G01N 33/576

[52] U.S. Cl. ........................... 435/5; 435/7.21; 435/7.92; 436/518; 436/820

[58] Field of Search ............................. 435/5, 7.21, 7.92, 435/968; 436/518, 534, 540, 804, 820

[56] References Cited

U.S. PATENT DOCUMENTS 5,350,671 9/1994 Houghton et al. ......................... 435/5

FOREIGN PATENT DOCUMENTS 0 388 232 9/1990 European Pat. Off. .
463848 1/1992 European Pat. Off. .
0 472 207 2/1992 European Pat. Off. .
0 518 313 12/1992 European Pat. Off. .
WO 92/08734 5/1992 WIPO .

OTHER PUBLICATIONS

Proc. Natl. Acad. Sci. USA, vol. 88, pp. 2451–2455, Mar. 1991, Q. L. Choo, et al., "Genetic Organization and Diversity of the Hepatitis C Virus".

Viral Hepatitus and Liver Disease, Jun. 1, 1991, G. Kuo, et al., pp. 347–349, "Serodiagnosis of Hepatitus C Viral Infection Using Recombinant–Based Assays for Circulating Antibodies to Different Viral Proteins".

Virology, vol. 180, No. 2, Feb. 1, 1991, pp. 842–848, A.J. Weiner, et al., "Variable and Hypervariable Domains Are Found in the Regions of HCV Corresponding to the Flavivirus Envelope and NS1 Proteins and the Pestivirus Envelope Glycoproteins".

Hepatology, vol. 16, No. 4, 1992, p. 226 A. O. Yokosuka, et al., "Detection of Anti–Hepatitis C Virus E2/NS1 Antibody in Patients With Type C Liver Disease by Western Blotting".

Okamoto et al., The 5'–Terminal Sequence of the Hepatitis C Virus Genome, Japan J. Exp. Med. 60(3): 167–177, 1990.

Harada et al., Establishment of a cell line constitutively expressing E2 glycoprotein of hepatitis C virus and humoral response of hepatitis C patients to the expressed protein, J. Gen. Virol. 76:1223–1231, 1995.

Biochemical and Biophysical Research Communications, vol. 172, No. 2, pp. 511–516, Oct. 30, 1990, Kanae Muraiso, et al., "A Structural Protein of Hepatitis C Virus Expressed in *E. coli* Facilitates Accurate Detection of Hepatitus C Virus".

Proc. Natl. Acad. Sci. USA, vol. 88, pp. 4641–4645, Jun., 1991, Joe Chiba, et al., "Serodiagnosis of Hepatitis C Virus (HCV) Infection With an HCV Core Protein Molecularly Expressed by a Recombinant Baculovirus".

The Lancet, vol. 337, pp. 317–319, Feb. 9, 1991, C. L. Vander Poel, et al., "Confirmation of Hepatitis C Virus Infection By New Four–Antigen Recombinant Immunoblot Assay".

Journal of Clinical Microbiology, vol. 29, No. 11, pp. 2616–2617, R. K. Chaudhary, et al., "Evaluation of Hepatitis C Virus Kits".

Hepatology, vol. 15, No. 3, pp. 391–394, 1992, T. Katayama, et al., "Improved Serodiagnosis of Non–A, Non–B Hepatitus By an Assay Detecting Antibody To Hepatitis C Virus Core Antigen".

Hepatology, vol. 15, No. 2, pp. 350–353, 1992, H. J. Alter, M.D., "New Kit on the Block: Evaluation of Second–Generation Assays for Detection of Antibody To Hepatitis C Virus".

Hepatology, vol. 15, No. 2, pp. 187–190, 1992, L. J. Jeffers, et al., "Prevalence of Antibodies To Hepatitis C Virus Among Patients With Cryptogenic Chronic Hepatitis and Cirrhosis".

Hepatology, vol. 15, No. 2, pp. 180–186, 1992, N. Okamoto, et al., "Antibodies Against Synthetic Oligopeptides Deduced From the Putative Core Gene for Diagnosis of Hepatitis C Virus Infection".

Hepatology, vol. 15, No. 2, pp. 175–179, 1992, J. Brown, et al., "Seroprevalence of Hepatitis C Virus Nucleocapsid Antibodies In Patients With Cryptogenic Chronic Liver Disease".

Hepatology, vol. 15, No. 1, pp. 19–25, 1992, J. G. McHutchison, et al., "Improved Detection of Hepatitis C Virus Antibodies In High–Risk Populations".

Proc. Natl. Acad. Sci. USA, vol. 89, pp. 4486–4489, May, 1992, G. J. Kotwal, et al., "Detection of Acute Hepatitis C Virus Infection By Elisa Using a Synthetic Peptide Comprising a Structural Epitope".

(List continued on next page.)

*Primary Examiner*—Marian C. Knode
*Assistant Examiner*—Donna C. Wortman
*Attorney, Agent, or Firm*—Oblon, Spivak, McClelland, Maier & Neustadt, P.C.

[57] ABSTRACT

A diagnostic reagent for hepatitis C, which detects an antibody induced by infection of hepatitis C virus, and comprises the second envelope protein or first non-structural protein which is encoded by the gene of hepatitis C virus and has a sugar chain. This invention also provide a method for detecting an anti-hepatitis C virus antibody. The use of the diagnostic reagent for hepatitis C according to the present invention makes highly sensitive diagnosis of hepatitis C possible.

12 Claims, 6 Drawing Sheets

OTHER PUBLICATIONS

Proc. Natl. Acad. Sci. USA, vol. 89, pp. 3190–3194, Apr., 1992, Wei–Mei Ching, et al., "Interaction of Immune SERA With Synthetic Peptides Corresponding To the Structural Protein Region of Hepatitis C Virus".

Journal of Clinical Microbiology, vol. 30, No. 3, pp. 552–556, Mar., 1992, D. S. Vallari, et al., "Serological Markers of Posttransfusion Hepatitis C Viral Infection".

Journal of Virology, vol. 66, No. 3, pp. 1425–1431, Mar., 1992, Y. Matsuura, et al., "Expression of Processed Envelope Protein of Hepatitis C Virus in Mammalian and Insect Cells".

Biochemical and Biophysical Research Communications, vol. 183, No. 3, pp. 925–930, Mar. 31, 1992, Eiji Mita, et al., "Expression of MBP–HCV NS1/E2 Fusion Protein in *E. coli* and Detection of Anti–NS1/E2 Antibody In Type C Chronic Liver Disease".

Hepatology, vol. 14, No. 5, pp. 756–762, 1991, Anna S. F. Lok, et al., "Overestimation of the Prevalence of Antibody To Hepatitis C Virus In Retrospective Studies On Stored Sera".

Hepatology, vol. 14, No. 2, pp. 381–388, 1991, M. Houghton, et al., "Molecular Biology of the Hepatitis C Viruses: Implications for Diagnosis, Development and Control of Viral Disease".

Hepatology, vol. 14, No. 1, pp. 38–43, 1991, J. A. Quiroga, et al., "IgH Antibody to Hepatitis C Virus In Acute and Chronic Hepatitis C".

Science, vol. 244, pp. 362–364, Apr. 21, 1989, G. Kuo, et al., "An Assay for Circulating Antibodies to a Major Etiologic Virus of Human Non–A, Non–B Hepatitus".

clone 1325

Bam HI
Kpn I
Eco RI
Bam HI
Xba I
Hin dIII
Ori
pUC 1325
Amp^r
Hin dIII digestion
Bam HI partial digestion
T4 DNA polymerase
Spe I linker ligation
Xba I digestion
Spe I linker
Bam HI
Xba I
Adapter ligation
Eco RI
Spe I linker
Bam HI
Kpn I
1325 SK ATG Hgi AI Dra III
codon
sp
polyA
Tth111I
R
EP
pSR 316
Ori
Ap^r
EP: SV40 early promoter
R: segment of HTLV-1 LTR
sp: SV40 late splicing sequence
polyA: SV40 late polyadenylation signal
EP
Sal I
pmoRH
Sal I
EP
Sal I
Eco RI
J. Virology 65, 6, 3015-3021, (1991)
Tth111I
T4 DNA polymerase
Gene 71, 19-27, (1988)
Sal I
EcoR I
T4 DNA polymerase
(Sal I) (Eco RI)
Bgl II linker
ligation
ATG Hgi AI Dra III
codon
sp
polyA
Bgl II
EP
R
EP
pSR 316EP
Ori
Ap^r $Ap^r$ Hgi AI Dra III T4 DNA polymerase Not I linker ligation ATG codon
Not I linker
sp
polyA
EP
R
EP
pSRNot
Ori
Ap^r
Eco RI
Bam HI
Kpn I
Spe I linker
Not I
T4 DNA polymerase
Kpn I
1325 SK
ligation
HCV clone 1325
sp
polyA
R
Sfi I
EP
Sfi I
EP
paSR1325X-3
Ori
Ap^r HCV
clone 1325
sp
polyA
R
Sfi I
EP
Sfi I
EP
paSR1325X-3
Ori
Ap^r
Sfi I
polylinker region
Ap^r
neo
pHLpl
cos
Sfi I
hmB
Sfi I
R
sp
HCV
polyA
Sfi I
Sfi I
ligation
neo
Ap^r
mulcos
pHL16SR1325
Ori
hmB
Sfi I
SRα
13
HCV NSI 25
Sfi I
X 16

DIAGNOSTIC REAGENT FOR HEPATITIS C

This application is a Continuation of application Ser. No. 07/956,993, filed on Oct. 6, 1992, now abandoned.

BACKGROUND OF THE INVENTION

This invention relates to a diagnostic reagent for hepatitis C comprising an antigen protein translated from a genome of hepatitis C virus. More specifically, this invention relates to a diagnostic reagent for detecting an antibody against hepatitis C virus (hereinafter referred to as "HCV"), which comprises a protein encoded by a gene of HCV, wherein said protein is identified as a glycoprotein called the second envelope protein or the first non-structural protein (hereinafter referred to as "E2/NS1").

The first successful cloning of human hepatitis virus which had been called non-A, non-B hepatitis virus was accomplished in 1988 by Chiron Co., Ltd. U.S.A and the hepatitis virus was designated HCV. Further, Chiron Co., Ltd. succeeded in expressing in a yeast a fused protein which comprises at the C-terminal the polypeptide corresponding to the region having 363 amino acid residues from the third nonstructural protein (NS3) to the fourth non-structural protein (NS4) both of which are portions of nonstructural proteins of HCV and at the N-terminal human superoxide dismutase(European unexamined patent publication No. 318216) and, using this recombinant antigen, developed a diagnostic reagent for hepatitis C (Science, 244, 359–362, 362–364, (1989)).

In Japan, the Japanese Red Cross Society has been using the diagnostic reagent in the screening of blood provided by donors, which is known as "C100-3 antibody test," in order to avoid post-transfusion hepatitis since the end of 1989. However, since not all samples are effectively screened only by C100-3 antibody test, post-transfusion hepatitis is not completely avoided.

Subsequently, further investigation of HCV genomes derived from the serum of a Japanese patient by the cloning technique revealed that HCV prevailed in Japan is similar to HCV obtained by Chiron Co., Ltd. but a different strain (Protein, Nucleic acid and Enzyme,36, 1679–1691, (1991)). In addition, the use of the core protein (C) region of the structural protein, the third non-structural protein (NS3) region, the fifth non-structural protein region and the like have been proposed as more effective diagnostic reagents than C100-3 (Lancet, 337, 317–319, 1991 and Japanese unexamined patent publication (hereinafter referred to as "J. P. KOKAI") No. Hei 3-103180).

The C100-3 antibody test system has a disadvantage that the detection rate and the sensitivity are low as mentioned above. Although proteins derived from C, NS3 and NS5 regions have been proposed as more effective antigens for detection than C100-3, any satisfactory results have not yet been reported. Therefore, there is a need for a diagnostic reagent and a diagnostic method for hepatitis C, having a higher detection rate and sensitivity.

SUMMARY OF THE INVENTION

The inventors have conducted various investigations to obtain a diagnostic reagent for hepatitis C, having a higher detection rate and sensitivity. As a result, they have found that E2/NS1 protein having a sugar chain, which is obtained by expressing cDNA of E2/NS1 region in animal cells reacts with the serum of the patient of hepatitis C with a high rate in a fluorescent antibody test and accomplished the goals of the present invention. The high reaction rate of E2/NS1 region with the serum of the patient of hepatitis C was unexpected because the protein derived from E2/NS1 region is susceptible to the mutation of an amino acid sequence and, therefore, the protein expressed in *E. coli* has been considered to react with the serum of the patient of hepatitis C with a lower rate comparing with the proteins derived from the other regions of HCV and it has not been expected to use the protein for a diagnostic reagent.

The present invention provides a diagnostic reagent for hepatitis C, which detects an antibody induced by infection of hepatitis C virus, characterised in that said diagnostic reagent comprises the second envelope protein or the first non-structural protein which is encoded by the genome of hepatitis C virus and has a sugar chain.

DETAILED EXPLANATION OF THE INVENTION

Figure 1:
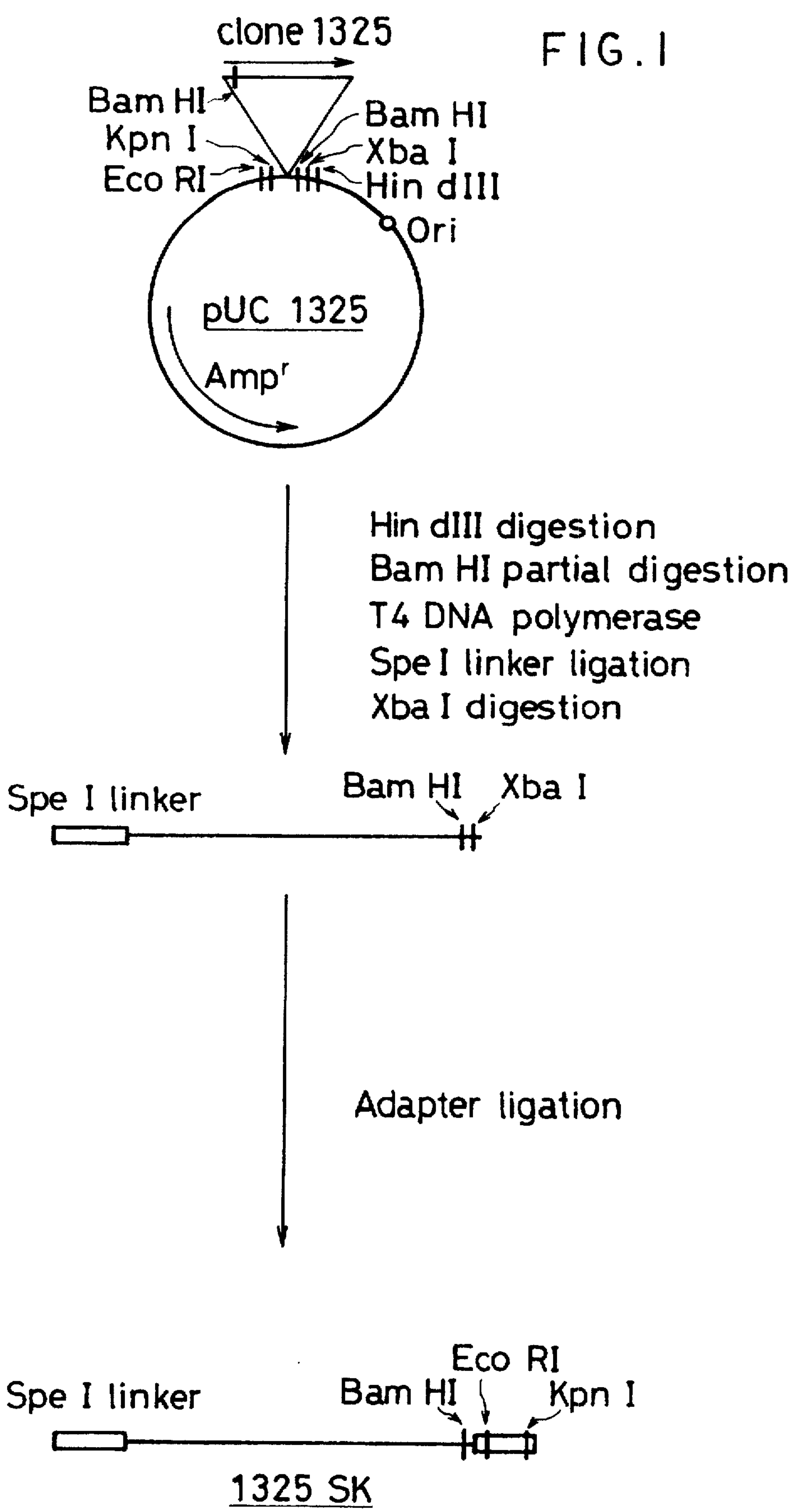
FIG. 1 shows the steps of constructing DNA fragment 1325SK containing the base sequence of clone J1-1325.

E2/NS1 protein of the present invention is a protein derived from the region called the second envelope protein or the first nonstructural protein, which is encoded by the genome of HCV. Examples of the proteins are illustrated in SEQUENCE ID Nos. 2, 4, 5, 7, 11, 13, 15, 17, 19, 21, and 22 in the SEQUENCE LISTING. Proteins obtained from such proteins by deleting, inserting, modifying or adding a part of amino acids are encompassed in the scope of the present invention provided that they maintain the reactivity with the serum of the patient of hepatitis C.

(1) Method of preparing clones of cDNA derived from the serum of the patient of hepatitis C, which are shown in SEQUENCE ID Nos. 1–5 of SEQUENCE LISTING and determining the base sequence thereof Genes or DNA fragments coding for novel polypeptides, which are shown in SEQUENCE ID Nos. 2, 4 and 5 of SEQUENCE LISTING can be prepared, for example, by a method described below.

Since there exists a trace of HCV in the serum and the genome of HCV is expected to be RNA, it was expected that cloning by Okayama-Berg method or Gubler-Hoffman method of the prior art would be attended by difficulties and, therefore, the following method was conducted to ensure the cloning of the gene susceptible to mutation from a trace of the serum.

The nucleic acid is extracted from the serum of the patient of hepatitis C as described in Example 1 later. Generally, it is preferred to use the serum having an OD value of 3.5 or more measured by a test kit of Ortho Inc. However, the present invention is not limited to the use of the serum having such an OD value. The serum is preferably mixed with transfer RNA (tRNA) as a carrier of virus RNA. The carrier is not limited to tRNA. Any polyribonucleoside can be used as carriers. If tRNA is used, there is an advantage that it can be rapidly confirmed by electrophoresis whether there is a required amount of tRNA having an intact length. By this confirmation, it can also be confirmed whether virus RNA degrades after being mixed with tRNA as a carrier of virus RNA. As a technique of cloning cDNA from the nucleic acid, it is preferred to use polymerase chain reaction method developed by Saiki et al. (PCR method, Nature, 324, 126, (1986)). First of all, a reverse transcriptase is reacted using virus RNA as a template. In the reaction, any commercially available random primers or synthesized DNA having a base sequence similar to that of primer AS1 which is shown below may be used as a primer.

5' 3' SEQUENCE ID NO. 23
AS1:GCTATCAGCAGCATCATCCA

A few bases at the 5' end of these sequences may be changed to other bases. Preferably, a few bases within 10 bases from the 5' end and more preferably, a few bases within 5 bases from the 5' end may be changed to other bases. In addition, 4–5 bases, preferably a few bases 10 may be deleted from the sequences at the 5' end of these sequences. Furthermore, any 8–12 bases, preferably 5–6 bases, more preferably a few bases, may be added to the sequences at the 5' end of these sequences.

PCR method is specifically carried out under the conditions described in Example 1. PCR method is carried out as described in Example 1 using the first complementary DNA (1st cDNA) thus obtained as a template to prepare a desired DNA fragment. The conditions of PCR method are suitably selected depending on the circumstances. Representative examples of sense primers include the following one:

5' 3' SEQUENCE ID NO. 24
S1:CAGITAITCCGGATCCCICAAG

"I" appearing in the sequence means inosine. A few bases at the 5' end of these sequences may be changed to other bases. Preferably, a few bases within 10 bases, more preferably, within 5 bases from the 5' end may be changed to other bases. In addition, 4–5 bases, preferably a few bases may be deleted from the sequences at the 5' end of these sequences. Furthermore, any 8–12 bases, preferably 5–6 bases, more preferably a few bases may be added to the sequences at the 5' end of these sequences.

The DNA fragment thus obtained is inserted at one of cloning sites such as Sma I site of a cloning vector such as pUC19 according to conventional technique. Using a plasmid having this DNA fragment, the base sequences of at least 3 clones are determined independently regarding both strands. The determination of the base sequences can be easily carried out by a dideoxy method using, for example, 7-deaza sequence kit availble from Takara Shuzo Co.,Ltd. or fluorescence sequencer GENESIS 2000 system available from Du Pont according to the protocol thereof. When the DNA fragment has a site which is considered difficult to determine the base sequence or has more than about 180 base pairs, a subcloning may be carried out according to conventional technique. SEQUENCE ID Nos. 2, 4, and 5 of SEQUENCE LISTING show the amino acid sequences of the proteins assumed from the base sequences of the DNA fragments thus determined.

Clone J1-1325 (SEQUENCE ID No. 2), clone N27, clone N19, H19 and Y19 (SEQUENCE ID No. 5) were prepared with the serums of different patients. Clone MX24 (SEQUENCE ID No.5) was prepared with a pool of the serums of the patients of hepatitis C. The clones shown in SEQUENCE ID Nos. 2, 4, and 5 which were prepared using a combination of primer S1 with primer AS1 correspond to the same region in the gene of HCV.

Antigen proteins derived from E2/NS1 protein regions shown in SEQUENCE ID Nos. 7, 9, 11, 13, 15, 17, 19, 21 and 22of SEQUENCE LISTING can also be used in the present invention.

The antigen protein of SEQUENCE ID No.7 can be obtained by expressing cDNA described in Journal of Virology, 65, 1105–1113, (1991). The antigen protein of SEQUENCE ID No.9 can be obtained by expressing cDNA described in Proceedings of the National Academy of Sciences of the U.S.A., 87, 9524–9528, (1990). The antigen protein of SEQUENCE ID No.4 can be obtained by expressing cDNA described in The fiftieth general meeting of Japanese Cancer Society, 379, (1991). The antigen protein of SEQUENCE ID No.13 can be obtained by expressing cDNA described in European Patent No.0.388,232 (1990). The antigen proteins of SEQUENCE ID Nos.15 and 17 can be obtained by expressing cDNAs described in Proceedings of the National Academy of Sciences of the U.S.A., 88, 3392–3396, (1991). The antigen proteins of SEQUENCE ID Nos.19 and 21 can be obtained by expressing cDNAs described in Japanese Journal of Experimental Medicine, 60, 167–177, (1990). The antigen protein of SEQUENCE ID No.22 can be obtained by expressing cDNA described in 00 Biochemical and Biophysical Research Communications, 175, 220–228, (1991). The sequences shown in SEQUENCE ID Nos. 7, 9, 11, 13, 15, 17, 19, 21 and 22correspond to the same region as that of the sequences shown in SEQUENCE ID Nos.2, 4, and 5.

(2) Expression of polypeptides encoded by the clones prepared in step (1)

In order to produce E2/NS1 protein, it is necessary to select an appropriate host-vector system which is able to stably express the protein. Further, it is required that the expressed E2/NS1 protein has the same level of biological activity, that is, antigenicity as that of HCV. Considering that natural E2/NS1 protein is expected to be a glycoprotein and that E2/NS1 protein contains many cysteine residues and the positions of the thiol bonds between the cysteine residues and the higher-order structure of the protein are important to maintain the activity, it is desired to express the protein in such an animal cell host as CHO cell, COS cell, mouse L cell, mouse C127 cell and mouse FM3A cell, preferably CHO cell. When these cells are used as hosts, it is expected that processed E2/NS1 protein is produced by introducing E2/NS1 gene having a signal-like sequence of from the 32 position to the 44 position of the amino acid sequences shown in SEQUENCE ID Nos.2, 4, 5, 7, 9, 11, 13, 15, 17, 19, 21, and 22 into the cell. Expression plasmids for these animal host cells can be constructed as follows:

As promoters in the animal cells, one can use the active-type promoter of adenovirus EIA gene (Biochemical Experiment Lecture, second series, Vol. 1, Techniques for gene investigations II, 189–190 (1986)), the early promoter of SV40, the late promoter of SV40, the promoter of apolipoprotein E gene and SR α promoter (Molecular and Celluar Biology, 8, 466–472, (1988)), preferably the promoter of SV40 and SR α promoter.

A DNA fragment of a gene coding for E2/NS1 protein containing the signal-like sequence is inserted downstream of the promoter in a direction of the transcription. When the expression vector of E2/NS1 protein is constructed, a ligated gene fragment of at least two gene fragments coding for E2/NS1 protein may be inserted downstream of the promoter. At least two units of DNA fragments ligated upstream of the 5' end of the DNA fragment of the gene coding for E2/NS1 protein with such a promoter as that of SV40 may be ligated together in the same direction of the transcription and then inserted in the vector. Polyadenylation sequence is required to be present downstream of the gene coding for E2/NS1 protein. For example, at least one of polyadenylation sequences derived from SV40 gene, β-globin gene or metallothionein gene is required to be present downstream of the gene coding for E2/NS1 protein. When at least two of the DNA fragments containing the gene coding for E2/NS1 protein ligated to the promoter are ligated, the polyadenylation sequence may be present at each 3' end of the gene coding for E2/NS1 protein.

In transforming an animal cell such as CHO cell with this expression vector, the use of a selective marker is desired. Examples of the selective markers include DHFR gene expressing methotrexate resistance (Journal of Molecular Biology, 159, 601, (1982)), Neo gene expressing antibiotic G-418 resistance (Journal of Molecular Applied Genetics, 1, 327, (1982)), Ecogpt gene derived from *E. coli*, expressing mycophenol acid resistance (Proceedings of the National Academy of Sciences of the U.S.A., 78, 2072, (1981)), hph gene expressing antibiotic hygromycin resistance (Molecular and Celluar Biology, 5, 410, (1985)) and the like. A promoter such as the aforementioned promoter derived from SV40 and the promoter of TK gene of Herpes virus is inserted upstream of the 5' end of each drug resistance gene. The aforementioned polyadenylation sequence are contained downstream of the 3' end of each drug resistance gene. When such a drug resistance gene is inserted in the expression vector of E2/NS1 protein, it may be inserted downstream of the polyadenylated site in the gene coding for E2/NS1 protein in a right direction or a reverse direction. These expression vectors do not require any co-transfection with another plasmid containing a selective marker gene in preparing a transfect.

In the case where such a selective marker gene is not inserted in the expression vector of E2/NS1 protein, a vector having a selective marker of the transfect, such as pSV2neo (Journal of Molecular Applied Genetics, 1, 327, (1982)), PMBG (Nature, 294, 228, (1981)), pSV2gpt (Proceedings of the National Academy of Sciences of the U.S.A., 78, 2072, (1981)), pAd-D26-1 (Journal of Molecular Biology, 159, 601, (1982)) and the like may be used together with the expression vector of E2/NS1 protein to conduct co-transfection. The transfect can be easily selected by gene expression of the selective marker gene.

Examples of methods of introducing the expression vector into the animal cell include calcium phosphate method (Virology, 52, 456, (1973)) and electroporation method (Journal of Membrane Biology, 10, 279, (1972)). Calcium phosphate method is used in general.

The transfected animal cell can be cultured by a float culture or an adherent culture in the conventional manner. The cultivation can be conducted in a medium such as MEM, Ham, F-12 and the like in the presence of 5–10% of serum or a suitable amount of insulin, dexamethasone and transferrin or in the absence of serum. The animal cell expressing E2/NS1 protein can be detected by fluorescent antibody technique using the serum of the patient according to the conventional method. The cloning is carried out by limiting dilution according to the conventional method to establish a cell line stably producing E2/NS1 protein.

E2/NS1 protein derived from HCV gene, thus obtained can be used as HCV antigen which reacts immunologically with the serum containing HCV antibody and therefore, is useful for the confirmation or the detection of the presence of Anti-HCV antibody in samples including blood or serum. Examples of the immunoassays include RIA (radioimmunoassay), ELISA (enzyme-linked immunoadsorbent assay), fluorescent antibody technique, agglutination reaction including latex fixation, immuno precipitation and the like. In the detection, a labelled antibody is usually used. A labelling substance such as a fluorescent substance, a chemoluminescent substance, a radioactive substance, a dyeing substance and the like can be used. Accordingly, using the above E2/NS1 protein derived from HCV gene as an antigen, the diagnostic reagent for hepatitis C according to the present invention can be prepared.

The reagent containing the protein having a sugar chain, which is derived from E2/NS1 region according to the present invention makes the confirmation or the detection of the presence of anti-HCV antibody in samples including blood or serum possible. The use of the reagent according to the present invention makes highly sensitive diagnosis of hepatitis C possible.

The present invention will be explained in more detail with reference to the following non-limiting examples.

EXAMPLE 1

(1) Extraction of the nucleic acid from the serum of the patient of hepatitis C

Twenty-five milliliters of a Tris buffer (50 mM Tris-HCl (pH 8.0), 1 mM EDTA and 100 mM NaCl) were added to 10 ml of the serum of the patient of hepatitis C, which showed at least 3.5 of an OD value by a HCV EIA kit available from Ortho Inc. After being mixed, the mixture was centrifuged at 20,000×g at 20° C. for 20 minutes. The obtained supernatant was centrifuged at 100,000×g at 20° C. for additional 5 hours. One point five milliliters of a Protenase K solution (1% sodium dodecyl sulfate, 10 mM EDTA, 10 mM Tris-HCl (pH 7.5), 2 mg/ml Protenase K (available from Pharmacia Co.) and 6.6 μg of a yeast tRNA mixture) were added to the precipitate. After the precipitate was dissolved in the Protenase K solution, the obtained solution was maintained at 45° C. for 90 minutes. The mixture was subjected at least four times to a phenol/chloroform treatment which comprises the steps of adding an equivalent amount of phenol/chloroform, violently agitating and then centrifuging the mixture to collect an aqueous phase containing a nucleic acid. Then, a chloroform treatment was carried out at least 2 times. To the obtained aqueous phase, one-tenth amount of 3M sodium acetate or an equivalent amount of 4M ammonium acetate, and 2.5-fold volume of ethanol were added and the mixture was left to stand at −20° C. overnight or −80° C. for at least 15 minutes. The mixture was centrifuged at 35,000 rpm for 4 hours by a SW41Ti rotor (available from Beckmann Co.) to collect a nucleic acid as a precipitate.

(2) Synthesis of CDNA (2-1) Synthesis of an RNA sample

After the nucleic acid obtained in step (1) was dried, 30 μl of water and 10 μl of ribonuclease inhibitor (100 units/μl, available from Takara Shuzo Co., Ltd.) were added thereto to dissolve the nucleic acid. The following synthesis of cDNA was carried out using the obtained nucleic acid solution.

(2-2) Synthesis of cDNA using an anti-sense primer

To 2μl of the aqueous solution of the nucleic acid prepared in step (2-1), 1 μl of an anti-sense primer (synthesized DNA primer AS1; 15 pmoles/μl ), 2 μl of 10×RT buffer (100 mM Tris-HCl (pH 8.3) and 500 mM of KCl), 4 μl of 25 mM $MgCl_2$, 8 μl of 2.5 mM 4dNTP and 1 μl of water were added and the mixture was maintained at 65° C. for 5 minutes and at room temperature for 5 minutes. Subsequently, 1 μl of 25 units of a reverse transcriptase (available from Life Science Co.) and 1 μl of a ribonuclease inhibitor (100 units/μl, available from Takara Shuzo Co., Ltd.) were added to the mixture and then the resulting mixture was maintained at 37° C. for 20 minutes, then at 42° C. for 30 minutes and finally at 95° C. for 2 minutes. Immediately thereafter, the mixture was cooled to 0° C. (Synthesis of complementary DNA). The DNA having a specific sequence was amplified using 10 μl of the DNA sample according to Saiki's method (Nature, 324, 126, (1986)), so-called PCR method as follows:

Water was added to a mixture of 10 μl of the above DNA sample, 10 μl of 10×PCR buffer (100 mM of Tris-HCl (pH 8.3), 500 mM of KCl, 15 mM of $MgCl_2$, and 1% of gelatin), 8μl of 2.5 mM 4dNTP, 2 μl of the synthesized DNA primer used in the synthesis of the complementary DNA (150 pmoles/μl), 3 μl of a synthesized DNA primer corresponding to the DNA primer (15 pmoles/μl) (which is complementary to the synthesized DNA primer used in the synthesis of the complementary DNA, i.e., the aforementioned primer S1) to prepare 100 μl of an aqueous solution. After the solution was maintained at 95° C. for 5 minutes, it was cooled rapidly to 0° C . One minute after the cooling, the solution was mixed with 0.5 μl of Taq DNA polymerase (7 units/μl, Trade Name "AmpliTaqTM" available from Takara Shuzo Co., Ltd.) and then mineral oil was layered on the mixture. This sample was incubated on a DNA Thermal Cycler available from Perkin Elmer Cetus Co. at 95° C. for 1 minute, at 40°–55° C. for 1 minute, and at 72° C. for 1–5 minutes for 25 cycles. After the sample was incubated finally at 72° C. for 7 minutes, the reaction aqueous solution was subjected to a phenol/chloroform treatment and a precipitation treatment with ethanol to obtain amplified DNA fragments.

The above precipitation treatment with ethanol was carried out by mixing the aqueous phase with a one-tenth amount of 3M sodium acetate or an equivalent amount of 4M ammonium acetate together with a 2.5-fold volume of ethanol, centrifuging the mixture at 15,000 rpm at 4° C. for 15 minutes by a rotor having a radius of about 5 cm and drying the precipitate.

(3) Cloning of the amplified DNA fragments and Determination of the base sequences thereof At least 1 pmole of the DNA fragments obtained by the method described in step (2—2) was treated with T4 DNA polymerase (available from TOYOBO CO.,LTD) to make blunt ends (Molecular Cloning, 1982, Cold Spring Harbor Laboratory Press). After a phosphoric acid group was introduced into the DNA fragment at the 5' end with polynucleotidekinase (available from TOYOBO CO.,LTD) (Molecular Cloning, 1982, Cold Spring Harbor Laboratory Press), the DNA fragment was inserted at Sma I site present in the multicloning sites of pUC19 cloning vector using a ligation kit (available from Takara Shuzo Co., Ltd.).

The vector DNA prepared in the following procedure was used in the ligation in an amount of 5–10 ng.

pUC18 cloning vector was cleaved with restriction enzyme Sma I (available from TOYOBO CO.,LTD) and then subjected to a phenol/chloroform treatment and a precipitaion treatment with ethanol. Subsequently, this was treated with alkaline phosphatase (available from Boehringer Mannheim) to conduct the dephosphorylation at the 5' end (Molecular Cloning, 1982, Cold Spring Harbor Laboratory Press), followed by a phenol/chloroform treatment and a precipitation with ethanol. The competent cell of *E. coli* JM109 or DH5 (available from TOYOBO CO.,LTD) was transformed with the DNA prepared in the above procedure. The procedure of the transformation was according to the protocol of COMPETENT HIGH prepared by TOYOBO CO.,LTD. At least 20 transformants transformed with the pUC18 cloning vector having the DNA fragment obtained by the method described in step (2—2) using the combination of the aforementioned primers were prepared.

Plasmid DNA pUC1325 shown in FIG. 1 was prepared from the obtained transformant in the conventional method and the base sequence of the plasmid was determined by a 7-deaza sequence kit available from Takara Shuzo Co., Ltd. or a fluorescence sequencer GENESIS 2000 system available from Du Pont. Two kinds of synthesized primers, 5'd(GTAAAACGACGGCCAGT)3' (SEQUENCE ID No. 25) and 5'd(CAGGAAACAGCTATGAC) 3' (SEQUENCE ID No. 26) were used to determine a base sequence of the + strand and that of the – strand of the DNA fragment. The DNA fragment had the same base sequence as that shown in SEQUENCE ID No. 1 of SEQUENCE LISTING. The amino acid sequence shown in SEQUENCE ID No. 1 of SEQUENCE LISTING is encoded by the + strand of the gene derived from HCV and inserted in the plasmid of the transformant.

The amino acid sequence encoded by the DNA fragment obtained was compared with the reported sequences of hepatitis C viruses. In step (2-2) of Example 1, three clones were obtained from the serum of one patient. The determination of the base sequence of the clones reveals that the patient carries several kinds of viruses.

(4) Preparation of a plasmid expressing E2/NS1 protein

FIGS. 1–6show a procedure of preparing a plasmid expressing E2/NS1 protein.

(4-1) Preparation of DNA fragment 1325SK

The DNA fragment of clone 1325 contained in plasmid pUC1325 obtained in step (3) was inserted at Sma I site of pUC18 so that the fragment had KpnI site of pUC18 at the 5' end of the + strand of clone 1325 coding for E2/NS1 protein and Bam HI site of pUC18 at the 3' end. After complete digestion with restriction enzyme Hin dIII, the fragment was partially digested with restriction enzyme Bam HI to obtain a DNA fragment which was cleaved not at Bam HI site within the vector but only at another Bam HI site present in clone 1325. The DNA fragment contains from the Bam HI site present at the 5' end to the 3' end of clone 1325 which was the DNA fragment obtained in step (2—2), which was derived from the gene of HCV.

Subsequently, as shown in FIG. 1, the DNA fragment was treated with T4 DNA polymerase to make blunt ends. After being ligated with SpeI linker consisting of the sequence of 5' pGGACTAGTCC 3' (SEQUENCE ID No. 27) (available from New England Biolab Co.), the fragment was cleaved with restriction enzyme Xba I (the Xba I site of the fragment was derived from plasmid pUC18). The following adaptor was ligated to Xba I site at the 3' end to obtain DNA fragment 1325SK.

```
5' pCTAGAGAATTCGGTAC 3'        (SEQUENCE ID NO. 28)
3'     TCCTTAAGCp     5'
```

(4-2) Construction of plasmid pSRNot

Expression vector pAC316 reported in Journal of Virology, 65, 3015–3021, (1991) was cleaved with restriction enzyme Tth 111I at Tth111I site present at the 3' end of 3' poly A region. T4 DNA polymerase was acted on the cleaved vector to make blunt ends. The fragment between SalI site and Eco RI site of plasmid pmoRH (FIG. 2) reported by Ikeda et al (Gene, 71, 19–27, (1988)) was cut out and T4 DNA polymerase was acted on the fragment to make blunt ends.

Figure 2:
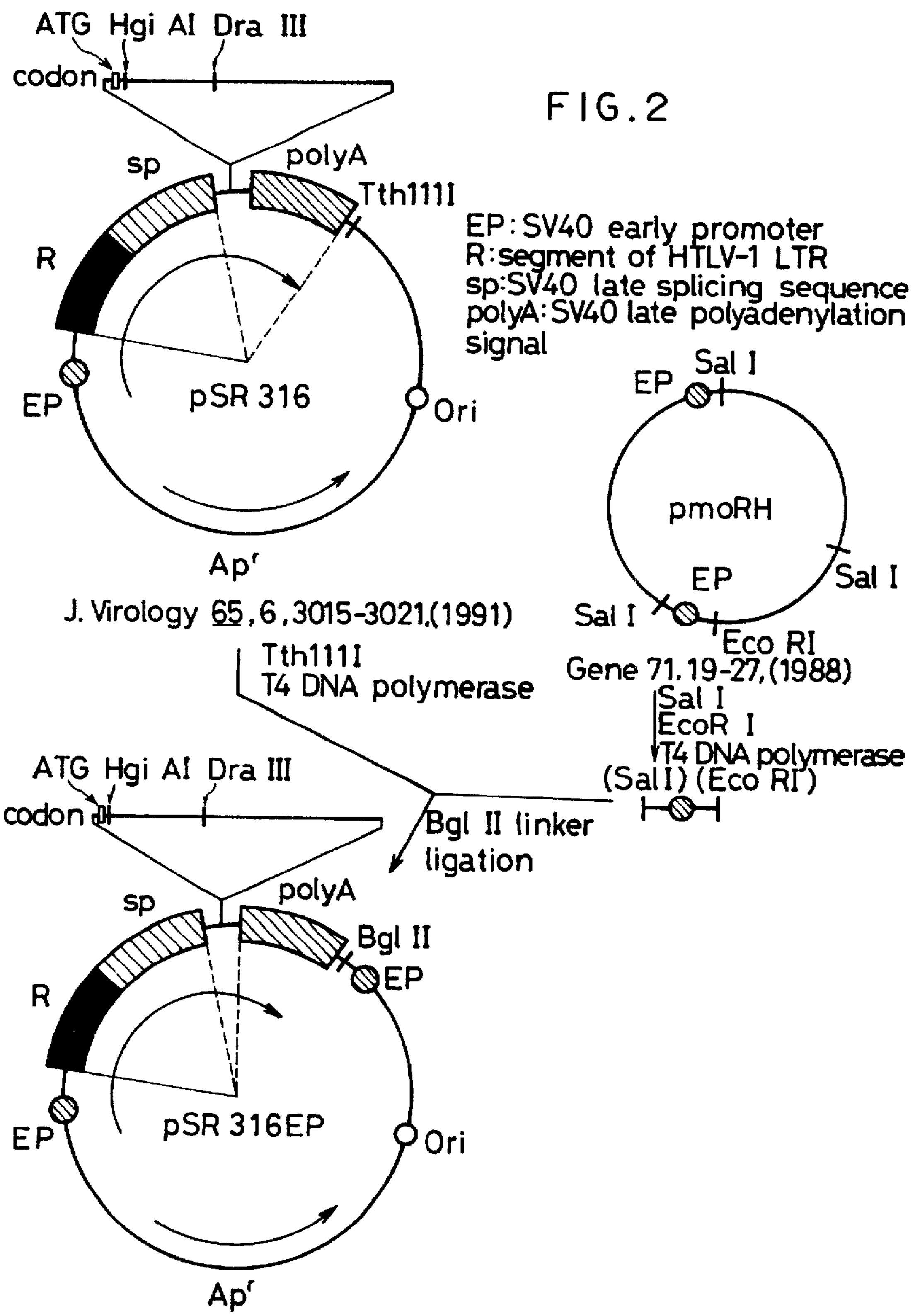
FIG. 2 shows the steps of constructing plasmid pSR316EP.

As shown in FIG. 2, the DNA fragment derived from pAC316 and the DNA fragment derived from pmoRH were ligated together with Bgl II linker (available from Takara Shuzo Co., Ltd.) to obtain plasmid pSR316EP containing one BglII linker and one DNA fragment containing the early promoter of SV40 derived from pmoRH. As shown in FIG.

Figure 3:
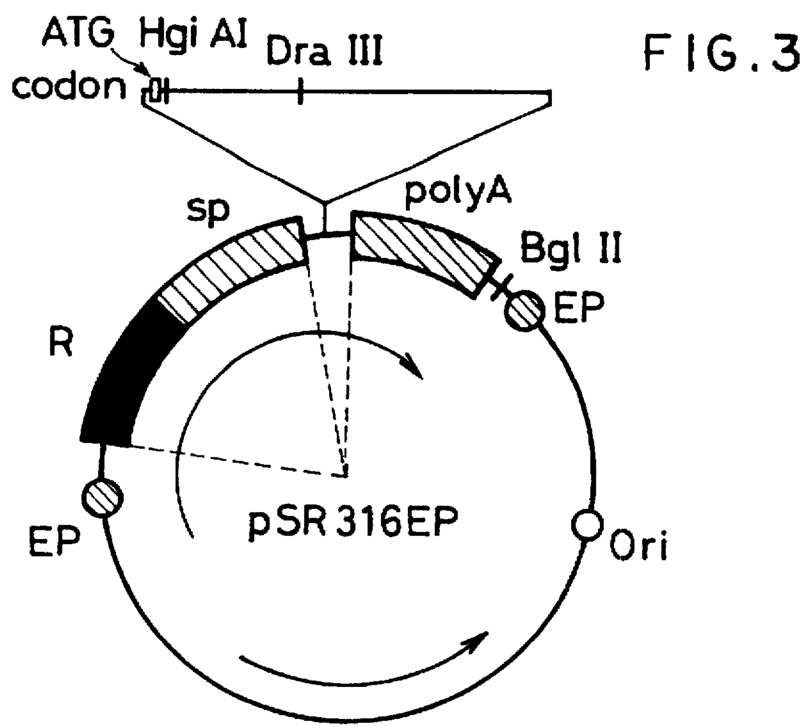
FIG. 3 shows the steps of constructing plasmid pSRNot.
Figure 3:
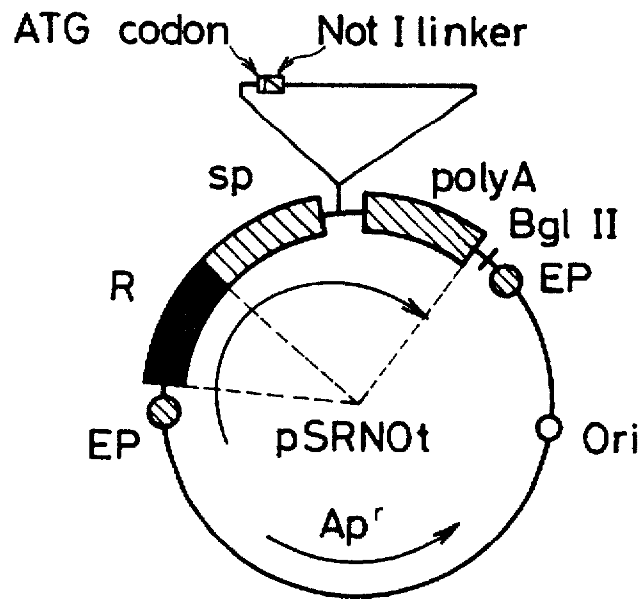

3, after plasmid pSR316EP was cleaved with restriction enzymes Hgi AI and Dra III, T4 DNA polymerase was acted on the plasmid to make blunt ends. Then, one Not I linker was introduced in the plasmid to obtain plasmid pSRNot (FIG. 3). Namely, NotI linker was prepared by synthesizing DNA having a sequence of 5' AGCGGCCGC 3' and phosphorylating the 5' end by kination (Molecular Cloning second edition, 11.31–11.44, (1989), Cold Spring Harbor Laboratory Press).

Figure 5:
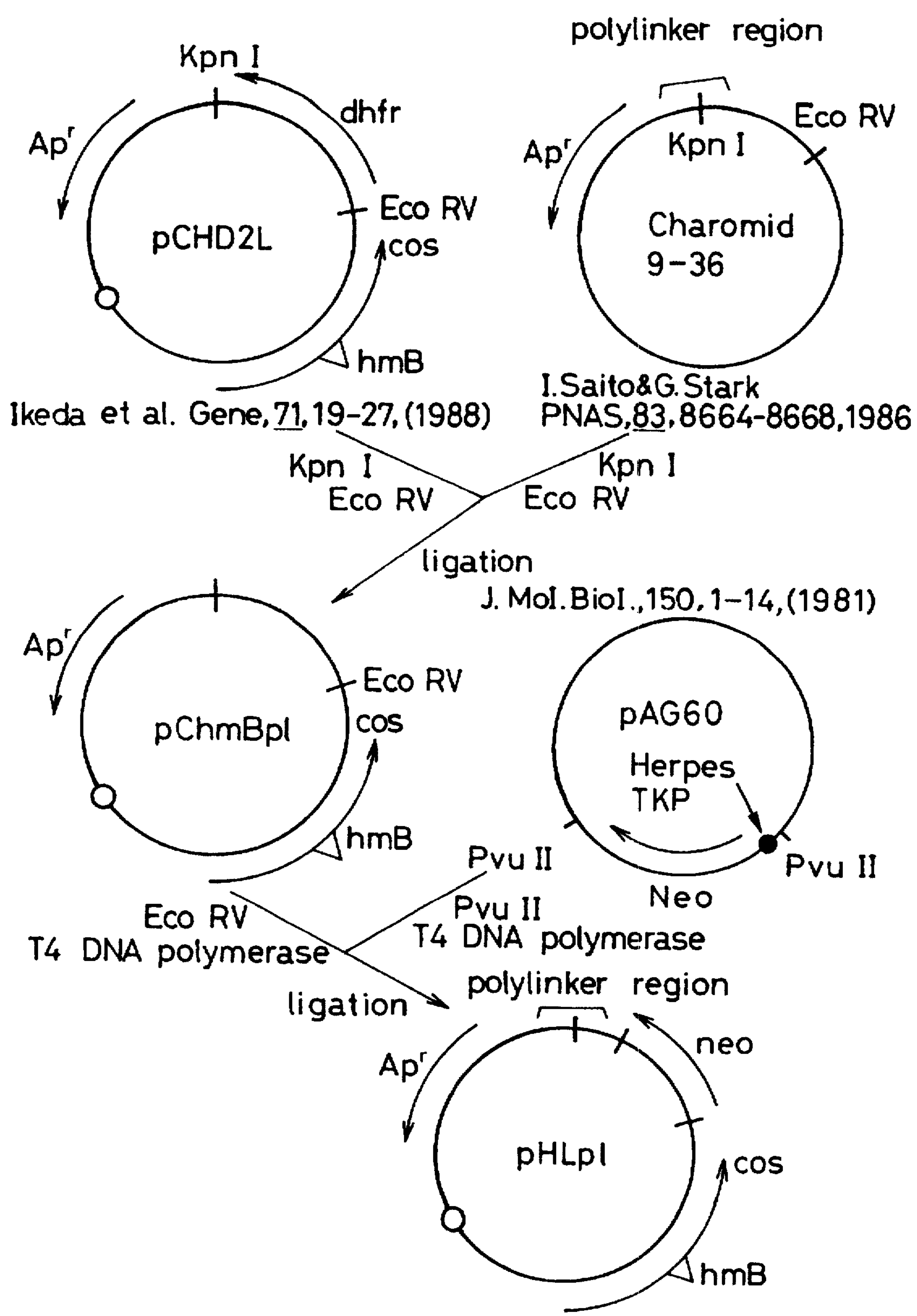
FIG. 5 shows the steps of constructing plasmid pHLp1.

Subsequently, dhfr gene was cut out from plasmid pCHD2L reported by Ikeda et al in Gene, 71, 19–27, (1988) using restriction enzymes Kpn I and Eco RV and Kpn I-EcoRV fragment of plasmid Charomid9–36 described in Proceedings of the National Academy of Sciences of the U.S.A., 83, 8664–8668, (1986) was inserted in the deleted dhfr gene region instead of the KpnI- EcoRV fragment coding for dhfr gene as shown in FIG. 5 to obtain plasmid pChmBp1. The plasmid contains a polylinker derived from plasmid Charomid9–36.

Then, plasmid pAG60 reported by Garapin et al. in Journal of Molecular Biology, 150 , 1–14, (1981) was cleaved with restriction enzyme Pvu II to obtain a Pvu II fragment coding for a neomycin gene. After plasmid pChmBp1 was cleaved with restriction enzyme Eco RV and then T4 DNA polymerase was acted to make blunt ends, the fragment obtained was ligated to the Pvu II fragment to obtain plasmid pHLp1 which contained the neomycin gene derived from plasmid pAG60 at the Eco RV site of plasmid pChmBp1 (FIG. 5).

(4-3) Construction of expression vector paSR1325X-3

Figure 4:
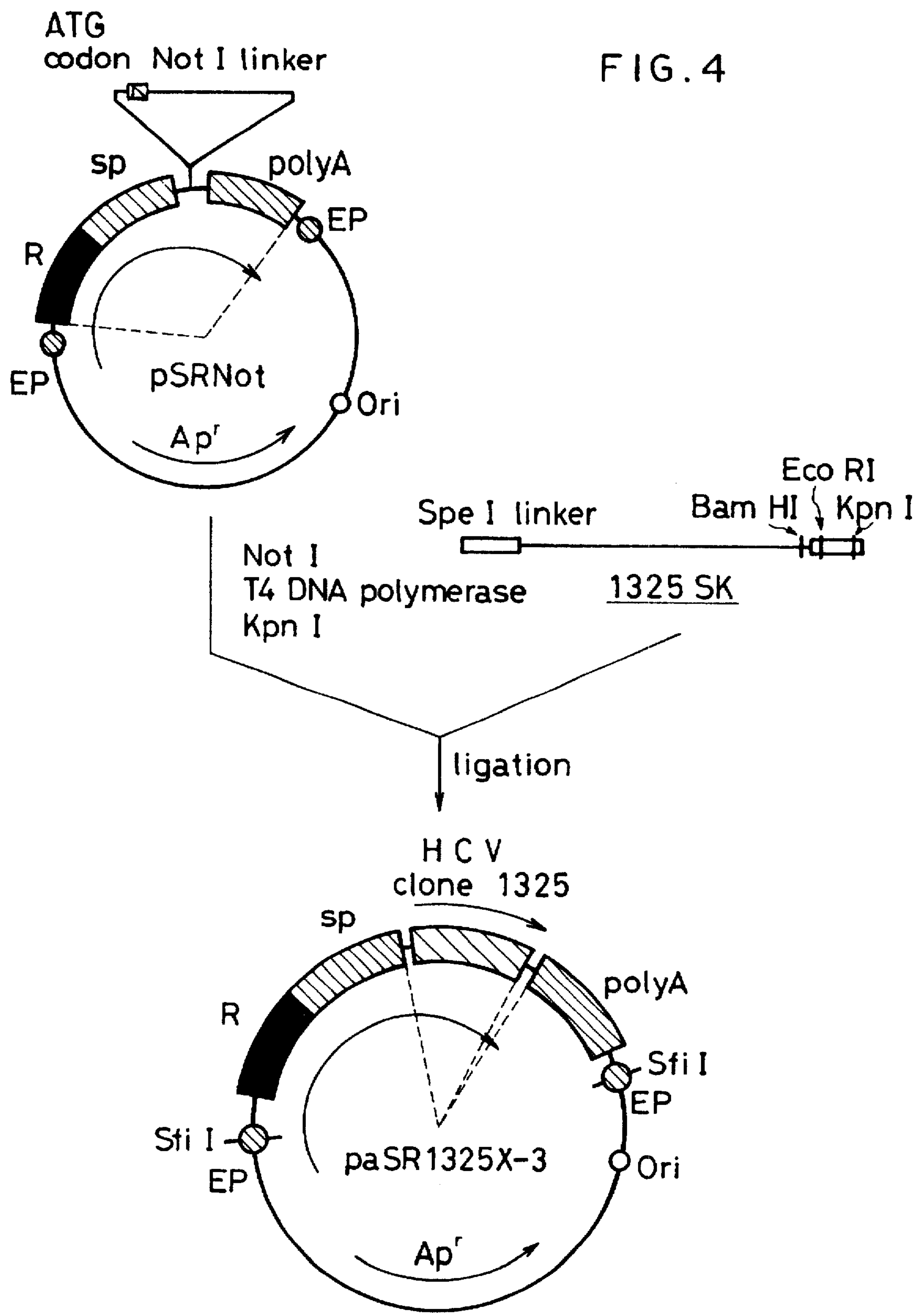
FIG. 4 shows the steps of constructing expression vector paSR1325X-3 having a DNA fragment coding for E2/NS1 protein.

As shown in FIG. 4, after plasmid pSRNot obtained in step (4-2) was cleaved with restriction enzyme Not I and then with T4 DNA polymerase to make blunt ends, this was cleaved with restriction enzyme Kpn I. The obtained DNA fragment was ligated to DNA fragment 1325SK obtained in step (4-1) to obtain expression vector paSR1325X-3 having only one DNA fragment 1325SK (FIG. 4).

(4-4) Construction of expression vector pHL16SR1325

Figure 6:
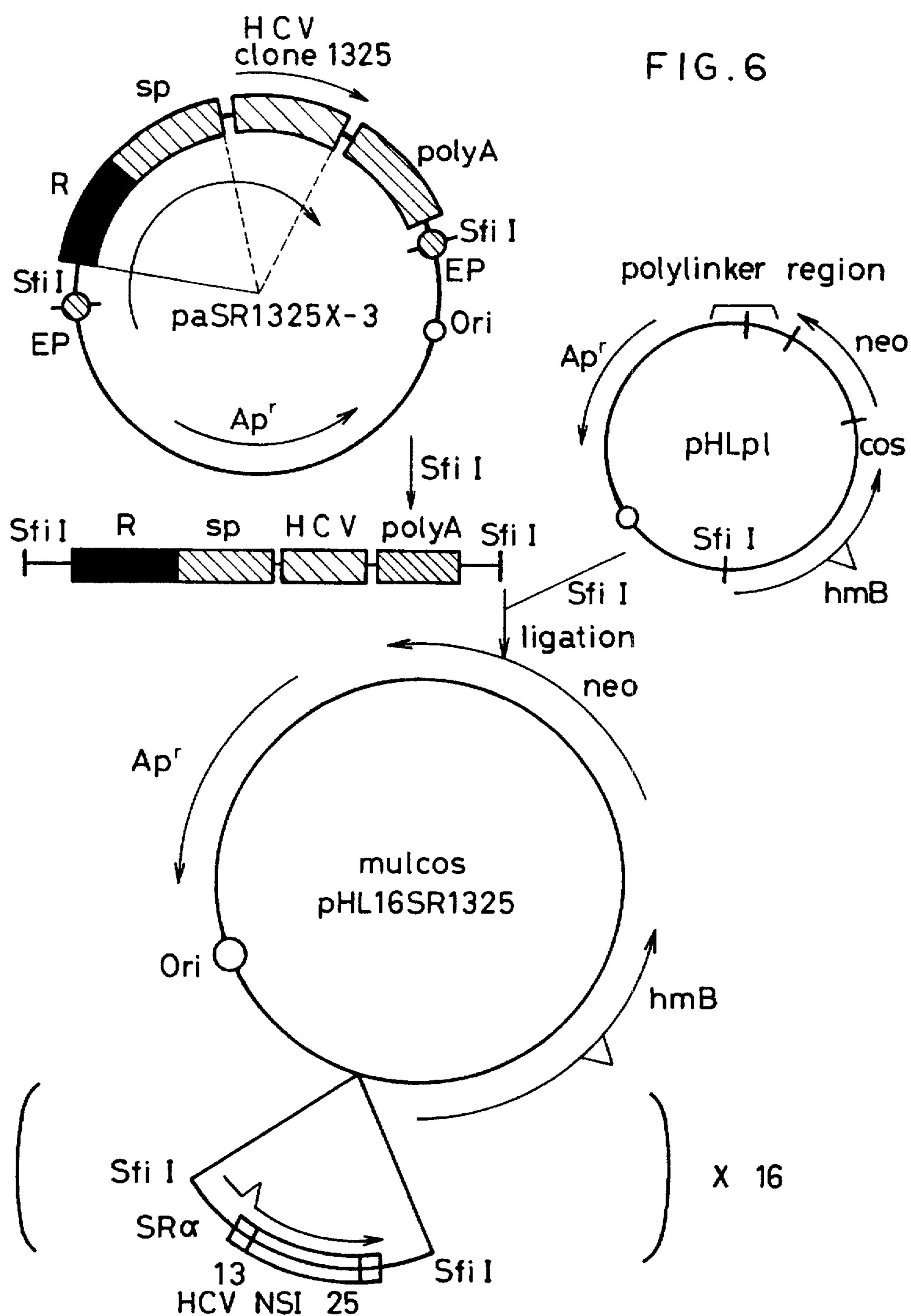
FIG. 6 shows the steps of constructing expression vector mulcos pHL16SR1325 having 16 DNA fragments coding for E2/NS1 protein.

As shown in FIG. 6, expression vector paSR1325X-3 obtained in step (4-3) was cleaved with restriction enzyme Sfi I to prepare two fragments one of which was an expression unit of clone 1325. The Sfi I sites were present in an initial promoter of SV40. Five μg of the Sfi I fragment having the expression unit of clone 1325 was ligated to 50 ng of the fragment obtained by cleaving expression vector pHLp1 with restriction enzyme Sfi I in 10 μl of a reaction solution using a ligation kit available from Takara Shuzo Co., Ltd. according to a protocol for the ligation kit to obtain expression vector pHL16SR1325 (FIG. 6).

The vector had successive sixteen DNA fragments 1325SK having at the Sfi I site of expression vector paSR1325X-3 the expression unit of clone 1325 which was a gene coding for E2/NS1 protein. In the vector, all of the DNA fragments 1325SK were inserted downstream of SV40 promoter of expression vector paSR1325X-3 in a direction of transcription.

(5) obtaining a cell line constantly expressing E2/NS1 protein

Expression vector pHL16SR1325 prepared in step (4) was recovered from the recombinant *E. coli* DH1 strain, purified according to the conventional technique described in Molecular Cloning second edition, 1989, Cold Spring Harbor Laboratory Press to obtain a large amount of the expression plasmid DNA. CHO cells were transfected with the plasmid DNA according to the method described in Ausubel et al. (Current Protocols in Molecular Biology, Greene Publishing Associates and Wiley-Interscience, Capter 9.1.1–9.1.4, (1987)) as follows:

CHO cells were cultured in Ham F-12 medium containing 10% of fetal calf serum (FCS) in a plate having a diameter of 6 cm until the cells were in semiconfluent condition. Then, the medium was removed from the plate and a DNA solution was dropwise added thereto. The DNA solution was previously prepared by the following procedure.

Three hundred μl of 2×HEBS solution (2×HEBS solution ; 1.6% sodium chloride, 0.074% potassium chloride, 0.05% $Na_2HPO_4.12H_2O$, 0.2% dextrose and 1% HEPES (pH 7.05)) were mixed with 10 μg of the plasmid DNA in each plate and sterilized water was added to the mixture to prepare a solution of 570 μl. The solution was charged in an Eppendorf centrifuge tube. The DNA solution was violently agitated by a Vortex mixer for 1–2 seconds while adding 30 μl of 2.5M calcium chloride solution thereto. The DNA solution was agitated by a Vortex mixer at about 10-minute intervals during being left to stand for 30 minutes. The obtained DNA solution was added to the aforementioned CHO cells and the CHO cells were left to stand at room temperature for 30 minutes. Then, 5 ml of Ham F-12 medium containing 10% of FCS available from GIBCO Co. were added to the plate and the culture was incubated at 37° C. under air containing 5% carbon dioxide for 4–5 hours. Subsequently, the medium was removed from the plate and the cells were washed with 5 ml of a 1×BS ++ solution (1×TBS ++ solution ; 25 mM Tris-HCl (pH 7.5), 140 mM sodium chloride, 5 mM potassium chloride, 0.6 mM disodium hydrogen phosphate, 0.08 mM calcium chloride and 0.08 mM magnesium chloride). After the 1×TBS ++ solution was removed, 5 ml of a 1×TBS ++ solution containing 20% of glycerol was added to the cells and the culture was left to stand at room temperature for 1–2 minutes. After the supernatant was removed from the plate, the cells were washed again with 5 ml of a 1×TBS ++ solution and cultured in 5 ml of fresh Ham F-12 medium containing 10% of FCS in the plate at 37° C. under air containing 5% carbon dioxide for 48 hours. Then, the medium was removed and the cells were washed with 5 ml of a 1×TBS ++ solution. The cells were treated with a trypsin-EDTA solution (available from Sigma Co.) and left to stand at room temperature for 30 seconds. Five minutes after the trypsin-EDTA solution was removed, the cells attached to the wall of the plate were peeled adding 5 ml of Ham F-12 medium containing 10% of FCS. The cells cultured in one plate having a diameter of 5 cm were divided in ten plates having a diameter of 9 cm and cultured in the plates containing drug G418 (G418 sulfate (GENETICIN) available from GIBCO Co.) in a concentration of 600 μg/ml. Ten days after the cultivation, grown cells having G418 resistance were isolated and cultured for about 7 days in 1 ml of Ham F-12 medium containing 10% of FCS in a 24 well titer plate each well of which has an area of about 3.1 $cm^2$.

A part of the cells were cultured on slide glass (Lab-Tek Chamber Slides, Nunc4808 available from Japan Inter Med Co.) overnight. After being rinsed with phosphate buffered saline (PBS), the slide glass was immersed in cold actone-methanol (1:1) solution and maintained at −20° C. for 15 minutes to fix the cells. The cells fixed on the slide glass were reacted with the serum of the patient of hepatitis C 20-fold diluted with PBS at 37° C. for 30 minutes. Then, the slide glass was washed three times with PBS for 5 minutes and reacted with FITC-labelled rabbit anti-human IgG (available from Daco Japan Co.) 50-fold diluted with PBS at 37° C. for 30 minutes. The slide glass was washed three times with PBS for 5 minutes and dried by putting the slide glass between two pieces of filter paper. After the slide glass was sealed with glycerin, the cells on the slide glass were observed under a fluorescence microscope. Screening positive cells as described above, successive three times of limiting dilution were carried out to establish cell line 13L20 constantly producing E2/NS1 protein.

(6) Study of the reactivity of 13L20 cells with the serum of the patient of hepatitis C After 13L20 cells established in step (5) were cultured on Lab-Tek Chamber Slides (Lab-Tek Chamber Slides, Nunc4808 available from Japan Inter Med Co.) overnight and then fixed with a cold acetone-methanol solution, the fixed cells were reacted with 59 serum samples of the patients of hepatitis C. Then, the cells were washed as described above and reacted with the secondary antibody. The observation under a fluorescence microscope revealed that 53 samples were positive. Among the 59 serum samples, 6 samples were judged to be positive using CHO cells constantly producing the first envelope region of HCV.

EXAMPLE 2

Using as a template the DNA fragment described in Example 11 (3) of the specification of European Patent Application No. 92109812.5 filed on Jun. 11, 1992 (TITLE OF THE INVENTION "Gene or DNA fragments derived from hepatitis C virus, polypeptides encoded thereby, and method of producing thereof"), PCR reaction was carried out in the same manner as that of Example 1 using the same primer to obtain a DNA fragment corresponding the same region as that of clone J1-1325 shown in SEQUENCE ID No. 1 of SEQUENCE LISTING. The region was a DNA fragment encoding for E2/NS1 protein like clone J1-1325. For example, using as a template the DNA fragment clone N27MX24A-1 having a base sequence shown in SEQUENCE ID No.3 of SEQUENCE LISTING described in the specification of the aforementioned European Patent Application filed on Jun. 11, 1992, plasmid pUCN27MX24A-2 was obtained. The base sequence of the DNA fragment coding for E2/NS1 protein, which was cloned in the plasmid is shown in SEQUENCE ID No. 3 of SEQUENCE LISTING. In addition, MK2724A2 cell line constantly producing E2/NS1 protein was established by the same procedure as that described in steps (4) and (5) of Example 1. The reactivity of the same samples as Example 1 with the cell line was estimated by the same method as that described in step (6) of Example 1. Results similar to those obtained in step (6) of Example 1 were obtained.

What is claimed is:

1. A method for detecting an anti-hepatitis C virus antibody, comprising the steps of:

contacting a sample with an animal cell expressing a second envelope/first non-structural protein, E2/NS1, of a hepatitis C virus under conditions which form an immunological complex between said protein and said anti-hepatitis C virus antibody, wherein said protein consists of an amino acid sequence selected from the group consisting of SEQUENCE ID Nos. 2, 4, 5, 7, 9, 11, 13, 15, 17, 19, 21 and 22; and detecting said immunological complex to confirm the presence of said anti-hepatitis C virus antibody in said sample.

2. The method according to claim 1, wherein the formation of the immunological complex is measured by radioimmunoassay, enzymes-linked immunoadsorbent assay, fluorescent antibody technique, agglutination reaction, or immune precipitation.

3. A method for detecting an anti-hepatitis C virus antibody, comprising the steps of:

contacting a sample with an animal cell expressing a second envelope/first non-structural protein, E2/NS1, of a hepatitis C virus under conditions which form an immunological complex between said protein and with said anti-hepatitis C virus antibody, wherein said protein consists of an amino acid sequence encoded by a base sequence selected from the group consisting of SEQUENCE ID Nos. 1, 3, 6, 8, 10, 12, 14, 16, 18 and 20; and detecting said immunological complex to confirm the presence of said anti-hepatitis C virus antibody in said sample.

4. The method of claim 3, wherein the formation of the immunological complex is measured by radioimmunoassay, enzyme-linked immunoadsorbent assay, fluorescent antibody technique, agglutination reaction, or immune precipitation.

5. A method for detecting an anti-hepatitis C virus antibody, comprising the steps of:

contacting a sample with a second envelope/first non-structural protein, E2/NS1, encoded by the gene of a hepatitis C virus and which has a sugar chain, said anti-hepatitis C virus antibody being specific to said second envelope/first non-structural protein, wherein said protein consists of an amino acid sequence selected from the group consisting of SEQUENCE ID Nos. 2, 4, 5, 7, 9, 11, 13, 15, 17, 19, 21 and 22; and detecting said anti-hepatitis C virus antibody.

6. The method of claim 5, wherein said second envelope/first non-structural protein is produced by an animal cell.

7. The method of claim 6, wherein said animal cell is a CHO cell.

8. A method for detecting an anti-hepatitis C virus antibody, comprising the steps of:

contacting a sample with a second envelope/first non-structural protein, E2/NS1, encoded by the gene of a hepatitis C virus and which has a sugar chain, said anti-hepatitis C virus antibody being specific to said second envelope/first non-structural protein, wherein said protein consists of an amino acid sequence encoded by a base sequence selected from the group consisting of SEQUENCE ID Nos. 1, 3, 6, 8, 10, 12, 14, 16, 18 and 20; and detecting said anti-hepatitis C virus antibody.

9. The method of claim 8, wherein said second envelope/first non-structural protein, E2/NS1, is produced by an animal cell.

10. The method of claim 9, wherein said animal cell is a CHO cell.

11. A method for detecting an anti-hepatitis C virus antibody, comprising the steps of:

contacting a sample with a second envelope/first non-structural protein, E2/NS1, of a hepatitis C virus under conditions which form an immunological complex between said protein and said anti-hepatitis C virus antibody, said protein having a sugar chain, wherein said protein consists of an amino acid sequence selected from the group consisting of SEQUENCE ID Nos. 2, 4, 5, 7, 9, 11, 13, 15, 17, 19, 21 and 22; and detecting said immunological complex to confirm the presence of said anti-hepatitis C virus antibody in said sample.

12. A method for detecting an anti-hepatitis C virus antibody, comprising the steps of:

contacting a sample with a second envelope/first non-structural protein, E2/NS1, of a hepatitis C virus under conditions which form an immunological complex between said protein and said anti-hepatitis C virus antibody, said protein having a sugar chain, wherein said protein consists of an amino acid sequence encoded by a base sequence selected from the group consisting of SEQUENCE ID Nos. 1, 3, 6, 8, 10, 12, 14, 16, 18 and 20; and detecting said immunological complex to confirm the presence of said anti-hepatitis C virus antibody in said sample.

* * * * *

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
( A ) LENGTH: 1207 base pairs
( B ) TYPE: nucleic acid
( C ) STRANDEDNESS: double
( D ) TOPOLOGY: linear ( i i ) MOLECULE TYPE: DNA (genomic)

( i v ) ANTI-SENSE: NO ( v i ) ORIGINAL SOURCE:
( A ) ORGANISM: Hepatitis C virus ( v i i ) IMMEDIATE SOURCE:
( B ) CLONE: J1-1325

( i x ) FEATURE:
( A ) NAME/KEY: CDS
( B ) LOCATION: 2..1207

( x i ) SEQUENCE DESCRIPTION: SEQ ID NO:1:

```
G ATC CCA CAA GCT GTC ATG GAC ATG GTG GCG GGG GCC CAC TGG GGA      46
  Ile Pro Gln Ala Val Met Asp Met Val Ala Gly Ala His Trp Gly
   1               5                  10                  15

GTC CTA GCG GGC CTT GCC TAC TAT TCC ATG GTG GGG AAC TGG GCT AAG    94
Val Leu Ala Gly Leu Ala Tyr Tyr Ser Met Val Gly Asn Trp Ala Lys
                20                  25                  30

GTT TTG ATT GTG ATG CTA CTC TTT GCC GGC GTT GAC GGG CAT ACC CGC   142
Val Leu Ile Val Met Leu Leu Phe Ala Gly Val Asp Gly His Thr Arg
            35                  40                  45

GTG ACG GGG GGG GTG CAA GGC CAT GTC ACC TCT ACA CTC ACG TCC CTC   190
Val Thr Gly Gly Val Gln Gly His Val Thr Ser Thr Leu Thr Ser Leu
        50                  55                  60

TTT AGA CCT GGG GCG TCC CAG AAA ATT CAG CTT GTA AAC ACC AAT GGC   238
Phe Arg Pro Gly Ala Ser Gln Lys Ile Gln Leu Val Asn Thr Asn Gly
    65                  70                  75
```

```
AGT TGG CAT ATC AAC AGG ACT GCC CTG AAC TGC AAT GAC TCC CTC AAA     286
Ser Trp His Ile Asn Arg Thr Ala Leu Asn Cys Asn Asp Ser Leu Lys
 80                  85                  90                  95

ACT GGG TTT CTT GCC GCG CTG TTC TAC ACA CAC AAG TTC AAC GCG TCC     334
Thr Gly Phe Leu Ala Ala Leu Phe Tyr Thr His Lys Phe Asn Ala Ser
                100                 105                 110

GGA TGC CCG GAG CGC ATG GCC AGC TGT CGC TCC ATT GAC AAG TTC GAC     382
Gly Cys Pro Glu Arg Met Ala Ser Cys Arg Ser Ile Asp Lys Phe Asp
            115                 120                 125

CAG GGA TGG GGT CCC ATC ACC TAT GCT CAA CCT GAC AAC TCG GAC CAG     430
Gln Gly Trp Gly Pro Ile Thr Tyr Ala Gln Pro Asp Asn Ser Asp Gln
        130                 135                 140

AGG CCG TAT TGC TGG CAC TAC GCA CCT CGA CAG TGT GGT ATC GTA CCC     478
Arg Pro Tyr Cys Trp His Tyr Ala Pro Arg Gln Cys Gly Ile Val Pro
    145                 150                 155

GCG TCG CAG GTG TGC GGT CCA GTG TAT TGC TTC ACC CCA AGC CCT GTT     526
Ala Ser Gln Val Cys Gly Pro Val Tyr Cys Phe Thr Pro Ser Pro Val
160                 165                 170                 175

GTA GTG GGG ACG ACC GAT CGT TTC GGC GCC CCT ACG TAT AAC TGG GGG     574
Val Val Gly Thr Thr Asp Arg Phe Gly Ala Pro Thr Tyr Asn Trp Gly
                180                 185                 190

GAC AAT GAG ACG GAC GTG CTG CTC CTA AAC AAC ACG CGG CCG CCG CAT     622
Asp Asn Glu Thr Asp Val Leu Leu Leu Asn Asn Thr Arg Pro Pro His
            195                 200                 205

GGC AAC TGG TTC GGC TGT ACA TGG ATG AAT AGC ACT GGG TTC ACC AAG     670
Gly Asn Trp Phe Gly Cys Thr Trp Met Asn Ser Thr Gly Phe Thr Lys
        210                 215                 220

ACG TGC GGA GGC CCC CCG TGT AAC ATC AGG GGG GTC GGC AAC AAC ACC     718
Thr Cys Gly Gly Pro Pro Cys Asn Ile Arg Gly Val Gly Asn Asn Thr
    225                 230                 235

TTG ACC TGC CCC ACG GAC TGC TTC CGG AAG CAC CCC GAC GCC ACT TAC     766
Leu Thr Cys Pro Thr Asp Cys Phe Arg Lys His Pro Asp Ala Thr Tyr
240                 245                 250                 255

ACA AAA TGT GGT TCG GGC CCT TGG TTG ACA CCT AGG TGC TTG GTT GAC     814
Thr Lys Cys Gly Ser Gly Pro Trp Leu Thr Pro Arg Cys Leu Val Asp
                260                 265                 270

TAC CCA TAC AGG CTC TGG CAC TAC CCC TGC ACT GTC AAC TTT ACC ATC     862
Tyr Pro Tyr Arg Leu Trp His Tyr Pro Cys Thr Val Asn Phe Thr Ile
            275                 280                 285

TTC AAG GTT AGG ATG TAT GTG GGG GGC GTG GAG CAC AGG CTT GAT GCT     910
Phe Lys Val Arg Met Tyr Val Gly Gly Val Glu His Arg Leu Asp Ala
        290                 295                 300

GCA TGC AAC TGG ACT CGA GGA GAG CGT TGC GAC TTG GAG GAC AGG GAT     958
Ala Cys Asn Trp Thr Arg Gly Glu Arg Cys Asp Leu Glu Asp Arg Asp
    305                 310                 315

AGA GCA GAG CTC AGC CCG CTA CTG CTG TCT ACG ACA GAG TGG CAG GTA    1006
Arg Ala Glu Leu Ser Pro Leu Leu Leu Ser Thr Thr Glu Trp Gln Val
320                 325                 330                 335

CTG CCC TGT TCC TTC ACC ACC CTA CCG GCT CTG TCC ACT GGT CTA ATC    1054
Leu Pro Cys Ser Phe Thr Thr Leu Pro Ala Leu Ser Thr Gly Leu Ile
                340                 345                 350

CAT CTC CAT CAG AAC GTC GTG GAC GTG CAA TAC CTG TAC GGT ATA GGG    1102
His Leu His Gln Asn Val Val Asp Val Gln Tyr Leu Tyr Gly Ile Gly
            355                 360                 365

TCA GCA GTT GTC TCC TTT GTA ATC AAA TGG GAG TAT GTC CTG TTG CTT    1150
Ser Ala Val Val Ser Phe Val Ile Lys Trp Glu Tyr Val Leu Leu Leu
        370                 375                 380

TTC CTT CTC CTG GCT GAC GCA CGC GTC TGT GCC TGC TTG TGG ATG ATG    1198
Phe Leu Leu Leu Ala Asp Ala Arg Val Cys Ala Cys Leu Trp Met Met
    385                 390                 395
```

```
CTG CTG ATA                                                                   1207
Leu Leu Ile
400
```

( 2 ) INFORMATION FOR SEQ ID NO:2:

( i ) SEQUENCE CHARACTERISTICS:
( A ) LENGTH: 402 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Ile Pro Gln Ala Val Met Asp Met Val Ala Gly Ala His Trp Gly Val
 1               5                  10                  15

Leu Ala Gly Leu Ala Tyr Tyr Ser Met Val Gly Asn Trp Ala Lys Val
            20                  25                  30

Leu Ile Val Met Leu Leu Phe Ala Gly Val Asp Gly His Thr Arg Val
        35                  40                  45

Thr Gly Gly Val Gln Gly His Val Thr Ser Thr Leu Thr Ser Leu Phe
    50                  55                  60

Arg Pro Gly Ala Ser Gln Lys Ile Gln Leu Val Asn Thr Asn Gly Ser
 65                  70                  75                      80

Trp His Ile Asn Arg Thr Ala Leu Asn Cys Asn Asp Ser Leu Lys Thr
                85                  90                  95

Gly Phe Leu Ala Ala Leu Phe Tyr Thr His Lys Phe Asn Ala Ser Gly
            100                 105                 110

Cys Pro Glu Arg Met Ala Ser Cys Arg Ser Ile Asp Lys Phe Asp Gln
        115                 120                 125

Gly Trp Gly Pro Ile Thr Tyr Ala Gln Pro Asp Asn Ser Asp Gln Arg
    130                 135                 140

Pro Tyr Cys Trp His Tyr Ala Pro Arg Gln Cys Gly Ile Val Pro Ala
145                 150                 155                     160

Ser Gln Val Cys Gly Pro Val Tyr Cys Phe Thr Pro Ser Pro Val Val
                165                 170                 175

Val Gly Thr Thr Asp Arg Phe Gly Ala Pro Thr Tyr Asn Trp Gly Asp
            180                 185                 190

Asn Glu Thr Asp Val Leu Leu Leu Asn Asn Thr Arg Pro Pro His Gly
        195                 200                 205

Asn Trp Phe Gly Cys Thr Trp Met Asn Ser Thr Gly Phe Thr Lys Thr
    210                 215                 220

Cys Gly Gly Pro Pro Cys Asn Ile Arg Gly Val Gly Asn Asn Thr Leu
225                 230                 235                     240

Thr Cys Pro Thr Asp Cys Phe Arg Lys His Pro Asp Ala Thr Tyr Thr
                245                 250                 255

Lys Cys Gly Ser Gly Pro Trp Leu Thr Pro Arg Cys Leu Val Asp Tyr
            260                 265                 270

Pro Tyr Arg Leu Trp His Tyr Pro Cys Thr Val Asn Phe Thr Ile Phe
        275                 280                 285

Lys Val Arg Met Tyr Val Gly Gly Val Glu His Arg Leu Asp Ala Ala
    290                 295                 300

Cys Asn Trp Thr Arg Gly Glu Arg Cys Asp Leu Glu Asp Arg Asp Arg
305                 310                 315                     320

Ala Glu Leu Ser Pro Leu Leu Leu Ser Thr Thr Glu Trp Gln Val Leu
                325                 330                 335
```

-continued

```
Pro Cys Ser Phe Thr Thr Leu Pro Ala Leu Ser Thr Gly Leu Ile His
            340                 345                 350

Leu His Gln Asn Val Val Asp Val Gln Tyr Leu Tyr Gly Ile Gly Ser
        355                 360                 365

Ala Val Val Ser Phe Val Ile Lys Trp Glu Tyr Val Leu Leu Leu Phe
    370                 375                 380

Leu Leu Leu Ala Asp Ala Arg Val Cys Ala Cys Leu Trp Met Met Leu
385                 390                 395                     400

Leu Ile
```

( 2 ) INFORMATION FOR SEQ ID NO:3:

( i ) SEQUENCE CHARACTERISTICS:
( A ) LENGTH: 1207 base pairs
( B ) TYPE: nucleic acid
( C ) STRANDEDNESS: double
( D ) TOPOLOGY: linear ( i i ) MOLECULE TYPE: DNA (genomic)

( i v ) ANTI-SENSE: NO ( v i ) ORIGINAL SOURCE:
( A ) ORGANISM: Hepatitis C virus ( v i i ) IMMEDIATE SOURCE:
( B ) CLONE: N27MX24A-2

( i x ) FEATURE:
( A ) NAME/KEY: CDS
( B ) LOCATION: 2..1207

( x i ) SEQUENCE DESCRIPTION: SEQ ID NO:3:

```
G ATC CCA CAA GCC GTG GTG GAT ATG GTG GCA GGG GCC CAC TGG GGA        46
  Ile Pro Gln Ala Val Val Asp Met Val Ala Gly Ala His Trp Gly
    1               5                  10                  15

GTC CTG GCG GGC CTT GCC TAC TAT TCC ATG GTG GGG AAC TGG GCT AAG      94
Val Leu Ala Gly Leu Ala Tyr Tyr Ser Met Val Gly Asn Trp Ala Lys
                 20                  25                  30

GTC TTG GTT GTG ATG CTG CTC TTC GCC GGT GTT GAC GGG GGG ACC CAC     142
Val Leu Val Val Met Leu Leu Phe Ala Gly Val Asp Gly Gly Thr His
             35                  40                  45

GTG ACA GGG GGG AAG GTA GCC TAC ACC ACC CAG GGC TTT ACA CCC TTC     190
Val Thr Gly Gly Lys Val Ala Tyr Thr Thr Gln Gly Phe Thr Pro Phe
         50                  55                  60

TTT TCA CGA GGG CCG TCT CAG AAA ATC CAA CTT GTA AAC ACT AAC GGC     238
Phe Ser Arg Gly Pro Ser Gln Lys Ile Gln Leu Val Asn Thr Asn Gly
     65                  70                  75

AGC TGG CAC ATC AAT AGG ACT GCC CTC AAT TGC AAT GAC TCC CTT AAC     286
Ser Trp His Ile Asn Arg Thr Ala Leu Asn Cys Asn Asp Ser Leu Asn
 80                  85                  90                  95

ACC GGG TTC CTT GCC GCG CTG TTC TAC ACC CAC AGC TTC AAC GCG TCC     334
Thr Gly Phe Leu Ala Ala Leu Phe Tyr Thr His Ser Phe Asn Ala Ser
                100                 105                 110

GGA TGT CCG GAG CGT ATG GCC GGT TGC CGC CCC ATT GAC GAG TTC GCT     382
Gly Cys Pro Glu Arg Met Ala Gly Cys Arg Pro Ile Asp Glu Phe Ala
            115                 120                 125

CAG GGG TGG GGT CCC ATC ACT CAT GTT GTG CCT AAC ATC TCG GAC CAG     430
Gln Gly Trp Gly Pro Ile Thr His Val Val Pro Asn Ile Ser Asp Gln
        130                 135                 140

AGG CCC TAT TGC TGG CAC TAC GCG CCT CGA CCG TGT GGT ATC GTA CCC     478
Arg Pro Tyr Cys Trp His Tyr Ala Pro Arg Pro Cys Gly Ile Val Pro
    145                 150                 155

GCG TCG CAG GTG TGT GGT CCG GTG TAT TGC TTC ACC CCA AGC CCT GTT     526
```

-continued

Ala Ser Gln Val Cys Gly Pro Val Tyr Cys Phe Thr Pro Ser Pro Val
160 165 170 175

GTG GTG GGG ACG ACC GAT CGT TTC GGC GCC CCC ACG TAC AAC TGG GGA 574
Val Val Gly Thr Thr Asp Arg Phe Gly Ala Pro Thr Tyr Asn Trp Gly
180 185 190

AAC AAT GAG ACG GAT GTG CTA CTC CTC AAC AAC ACA CGG CCG CCG CAG 622
Asn Asn Glu Thr Asp Val Leu Leu Leu Asn Asn Thr Arg Pro Pro Gln
195 200 205

GGC AAC TGG TTC GGT TGT ACC TGG ATG AAT GGC ACT GGG TTC ACA AAG 670
Gly Asn Trp Phe Gly Cys Thr Trp Met Asn Gly Thr Gly Phe Thr Lys
210 215 220

ACG TGC GGG GGC CCC CCG TGC AAC ATC GGG GGG GTC GGC AAC AAT ACC 718
Thr Cys Gly Gly Pro Pro Cys Asn Ile Gly Gly Val Gly Asn Asn Thr
225 230 235

TTG ACT TGC CCC ACG GAC TGC TTC CGG AAG CAC CCC GAG GCC ACT TAC 766
Leu Thr Cys Pro Thr Asp Cys Phe Arg Lys His Pro Glu Ala Thr Tyr
240 245 250 255

ACA AAA TGT GGT TCG GGG CCT TGG TTG ACG CCT AGG TGC CTA GTT CAT 814
Thr Lys Cys Gly Ser Gly Pro Trp Leu Thr Pro Arg Cys Leu Val His
260 265 270

TAC CCA TAC AGG CTC TGG CAC TAT CCC TGC ACT GTC AAC TTT ACC ATC 862
Tyr Pro Tyr Arg Leu Trp His Tyr Pro Cys Thr Val Asn Phe Thr Ile
275 280 285

TTC AAG GTT AGG ATG TAT GTG GGG GGC GTG GAA CAC AGG CTT GAA GCT 910
Phe Lys Val Arg Met Tyr Val Gly Gly Val Glu His Arg Leu Glu Ala
290 295 300

GCA TGC AAT TGG ACC CGA GGA GAG CGT TGT GAC TTG GAG GAC AGG GAT 958
Ala Cys Asn Trp Thr Arg Gly Glu Arg Cys Asp Leu Glu Asp Arg Asp
305 310 315

AGA TCA GAG CTT AGC CCG CTA TTG CTG TCC ACA ACA GAG TGG CAG GTA 1006
Arg Ser Glu Leu Ser Pro Leu Leu Leu Ser Thr Thr Glu Trp Gln Val
320 325 330 335

CTG CCC TGT TCC TTC ACC ACC CTG CCG GCT CTG TCC ACT GGT TTG ATT 1054
Leu Pro Cys Ser Phe Thr Thr Leu Pro Ala Leu Ser Thr Gly Leu Ile
340 345 350

CAT CTC CAT CAG AAC ATC GTG GAC GTG CAA TAT CTG TAC GGC ATA GGG 1102
His Leu His Gln Asn Ile Val Asp Val Gln Tyr Leu Tyr Gly Ile Gly
355 360 365

TCG GCG GTT GTC TCC TTC GCA ATC AAA TGG GAA TAT ATT CTG TTG CTT 1150
Ser Ala Val Val Ser Phe Ala Ile Lys Trp Glu Tyr Ile Leu Leu Leu
370 375 380

TTC CTC CTC CTG GCG GAC GCG CGC GTC TGT GCC TGC TTG TGG ATG ATG 1198
Phe Leu Leu Leu Ala Asp Ala Arg Val Cys Ala Cys Leu Trp Met Met
385 390 395

CTG CTG ATA 1207
Leu Leu Ile
400

( 2 ) INFORMATION FOR SEQ ID NO:4:

( i ) SEQUENCE CHARACTERISTICS:
( A ) LENGTH: 402 amino acids
( B ) TYPE: amino acid
( D ) TOPOLOGY: linear ( i i ) MOLECULE TYPE: protein ( x i ) SEQUENCE DESCRIPTION: SEQ ID NO:4:

Ile Pro Gln Ala Val Val Asp Met Val Ala Gly Ala His Trp Gly Val
1 5 10 15

Leu Ala Gly Leu Ala Tyr Tyr Ser Met Val Gly Asn Trp Ala Lys Val
20 25 30

-continued

Leu Val Val Met Leu Leu Phe Ala Gly Val Asp Gly Gly Thr His Val
35 40 45

Thr Gly Gly Lys Val Ala Tyr Thr Thr Gln Gly Phe Thr Pro Phe Phe
50 55 60

Ser Arg Gly Pro Ser Gln Lys Ile Gln Leu Val Asn Thr Asn Gly Ser
65 70 75 80

Trp His Ile Asn Arg Thr Ala Leu Asn Cys Asn Asp Ser Leu Asn Thr
85 90 95

Gly Phe Leu Ala Ala Leu Phe Tyr Thr His Ser Phe Asn Ala Ser Gly
100 105 110

Cys Pro Glu Arg Met Ala Gly Cys Arg Pro Ile Asp Glu Phe Ala Gln
115 120 125

Gly Trp Gly Pro Ile Thr His Val Val Pro Asn Ile Ser Asp Gln Arg
130 135 140

Pro Tyr Cys Trp His Tyr Ala Pro Arg Pro Cys Gly Ile Val Pro Ala
145 150 155 160

Ser Gln Val Cys Gly Pro Val Tyr Cys Phe Thr Pro Ser Pro Val Val
165 170 175

Val Gly Thr Thr Asp Arg Phe Gly Ala Pro Thr Tyr Asn Trp Gly Asn
180 185 190

Asn Glu Thr Asp Val Leu Leu Leu Asn Asn Thr Arg Pro Pro Gln Gly
195 200 205

Asn Trp Phe Gly Cys Thr Trp Met Asn Gly Thr Gly Phe Thr Lys Thr
210 215 220

Cys Gly Gly Pro Pro Cys Asn Ile Gly Gly Val Gly Asn Asn Thr Leu
225 230 235 240

Thr Cys Pro Thr Asp Cys Phe Arg Lys His Pro Glu Ala Thr Tyr Thr
245 250 255

Lys Cys Gly Ser Gly Pro Trp Leu Thr Pro Arg Cys Leu Val His Tyr
260 265 270

Pro Tyr Arg Leu Trp His Tyr Pro Cys Thr Val Asn Phe Thr Ile Phe
275 280 285

Lys Val Arg Met Tyr Val Gly Gly Val Glu His Arg Leu Glu Ala Ala
290 295 300

Cys Asn Trp Thr Arg Gly Glu Arg Cys Asp Leu Glu Asp Arg Asp Arg
305 310 315 320

Ser Glu Leu Ser Pro Leu Leu Leu Ser Thr Thr Glu Trp Gln Val Leu
325 330 335

Pro Cys Ser Phe Thr Thr Leu Pro Ala Leu Ser Thr Gly Leu Ile His
340 345 350

Leu His Gln Asn Ile Val Asp Val Gln Tyr Leu Tyr Gly Ile Gly Ser
355 360 365

Ala Val Val Ser Phe Ala Ile Lys Trp Glu Tyr Ile Leu Leu Leu Phe
370 375 380

Leu Leu Leu Ala Asp Ala Arg Val Cys Ala Cys Leu Trp Met Met Leu
385 390 395 400

Leu Ile ( 2 ) INFORMATION FOR SEQ ID NO:5:

( i ) SEQUENCE CHARACTERISTICS:

( A ) LENGTH: 402 amino acids ( B ) TYPE: amino acid ( D ) TOPOLOGY: unknown ( i i ) MOLECULE TYPE: protein ( v i ) ORIGINAL SOURCE:
( A ) ORGANISM: Hepatitis C virus ( v i i ) IMMEDIATE SOURCE:
( B ) CLONE: N27,N19,H19,Y19,MX24

( x i ) SEQUENCE DESCRIPTION: SEQ ID NO:5:

```
Ile Pro Gln Ala Val Val Asp Met Val Ala Gly Ala His Trp Gly Val
1               5                   10                  15

Leu Ala Gly Leu Ala Tyr Tyr Ser Met Val Gly Asn Trp Ala Lys Val
            20                  25                  30

Leu Val Val Met Leu Leu Phe Ala Gly Val Asp Gly Xaa Thr His Val
        35                  40                  45

Thr Gly Gly Lys Val Ala Tyr Thr Thr Gln Xaa Phe Thr Xaa Phe Phe
    50                  55                  60

Ser Arg Gly Pro Ser Gln Xaa Ile Gln Leu Val Asn Thr Asn Gly Ser
65                  70                  75                  80

Trp His Ile Asn Arg Thr Ala Leu Asn Cys Asn Asp Ser Leu Xaa Thr
                85                  90                  95

Gly Phe Leu Ala Xaa Leu Phe Tyr Xaa His Ser Phe Xaa Ala Ser Gly
            100                 105                 110

Cys Pro Glu Arg Met Ala Xaa Cys Arg Pro Ile Xaa Glu Phe Ala Gln
        115                 120                 125

Gly Trp Xaa Pro Ile Thr His Val Val Pro Xaa Xaa Ser Asp Gln Arg
    130                 135                 140

Pro Tyr Cys Trp His Tyr Ala Pro Arg Pro Cys Gly Xaa Val Pro Ala
145                 150                 155                 160

Xaa Gln Val Cys Gly Pro Val Tyr Cys Phe Thr Pro Ser Pro Val Val
                165                 170                 175

Val Gly Thr Thr Asp Arg Xaa Gly Ala Pro Thr Tyr Xaa Trp Gly Xaa
            180                 185                 190

Asn Glu Thr Asp Val Leu Leu Leu Asn Asn Thr Arg Pro Pro Gln Gly
        195                 200                 205

Asn Trp Phe Gly Cys Thr Trp Met Asn Gly Thr Gly Phe Thr Lys Thr
    210                 215                 220

Cys Gly Gly Pro Pro Cys Asn Ile Gly Gly Val Gly Asn Asn Thr Leu
225                 230                 235                 240

Thr Cys Pro Thr Asp Cys Phe Arg Lys His Pro Glu Ala Thr Tyr Thr
                245                 250                 255

Lys Cys Gly Ser Gly Pro Trp Leu Thr Pro Arg Cys Leu Val His Tyr
            260                 265                 270

Pro Tyr Arg Leu Trp His Tyr Pro Cys Thr Val Asn Phe Thr Ile Phe
        275                 280                 285

Lys Val Arg Met Tyr Val Gly Gly Val Glu His Arg Leu Glu Ala Ala
    290                 295                 300

Cys Asn Trp Thr Arg Gly Glu Arg Cys Asp Leu Glu Asp Arg Asp Arg
305                 310                 315                 320

Ser Glu Leu Ser Pro Leu Leu Leu Ser Thr Thr Glu Trp Gln Val Leu
                325                 330                 335

Pro Cys Ser Phe Thr Thr Leu Pro Ala Leu Ser Thr Gly Leu Ile His
            340                 345                 350

Leu His Gln Asn Ile Val Asp Val Gln Tyr Leu Tyr Gly Ile Gly Ser
        355                 360                 365

Ala Val Val Ser Phe Ala Ile Lys Trp Glu Tyr Ile Leu Leu Leu Phe
```

370 375 380

Leu Leu Leu Ala Asp Ala Arg Val Cys Ala Cys Leu Trp Met Met Leu
385 390 395 400

Leu Ile ( 2 ) INFORMATION FOR SEQ ID NO:6:

( i ) SEQUENCE CHARACTERISTICS:
( A ) LENGTH: 1207 base pairs
( B ) TYPE: nucleic acid
( C ) STRANDEDNESS: double
( D ) TOPOLOGY: linear ( i i ) MOLECULE TYPE: DNA (genomic)

( i v ) ANTI-SENSE: NO ( v i ) ORIGINAL SOURCE:
( A ) ORGANISM: Hepatitis C virus ( v i i ) IMMEDIATE SOURCE:
( B ) CLONE: BK164

( i x ) FEATURE:
( A ) NAME/KEY: CDS
( B ) LOCATION: 2..1207

( x i ) SEQUENCE DESCRIPTION: SEQ ID NO:6:

```
G ATC CCA CAA GCC GTC GTG GAC ATG GTG GCG GGG GCC CAC TGG GGA      46
  Ile Pro Gln Ala Val Val Asp Met Val Ala Gly Ala His Trp Gly
    1               5                  10                  15

GTC CTG GCG GGC CTT GCC TAC TAT TCC ATG GCG GGG AAC TGG GCT AAG      94
Val Leu Ala Gly Leu Ala Tyr Tyr Ser Met Ala Gly Asn Trp Ala Lys
                20                  25                  30

GTT CTG ATT GTG ATG CTA CTT TTT GCT GGC GTT GAC GGG GAT ACC CAC     142
Val Leu Ile Val Met Leu Leu Phe Ala Gly Val Asp Gly Asp Thr His
            35                  40                  45

GTG ACA GGG GGG GCG CAA GCC AAA ACC ACC AAC AGG CTC GTG TCC ATG     190
Val Thr Gly Gly Ala Gln Ala Lys Thr Thr Asn Arg Leu Val Ser Met
        50                  55                  60

TTC GCA AGT GGG CCG TCT CAG AAA ATC CAG CTT ATA AAC ACC AAT GGG     238
Phe Ala Ser Gly Pro Ser Gln Lys Ile Gln Leu Ile Asn Thr Asn Gly
    65                  70                  75

AGT TGG CAC ATC AAC AGG ACT GCC CTG AAC TGC AAT GAC TCT CTC CAG     286
Ser Trp His Ile Asn Arg Thr Ala Leu Asn Cys Asn Asp Ser Leu Gln
 80                  85                  90                  95

ACT GGG TTT CTT GCC GCG CTG TTC TAC ACA CAT AGT TTC AAC TCG TCC     334
Thr Gly Phe Leu Ala Ala Leu Phe Tyr Thr His Ser Phe Asn Ser Ser
                100                 105                 110

GGG TGC CCA GAG CGC ATG GCC CAG TGC CGC ACC ATT GAC AAG TTC GAC     382
Gly Cys Pro Glu Arg Met Ala Gln Cys Arg Thr Ile Asp Lys Phe Asp
            115                 120                 125

CAG GGA TGG GGT CCC ATT ACT TAT GCT GAG TCT AGC AGA TCA GAC CAG     430
Gln Gly Trp Gly Pro Ile Thr Tyr Ala Glu Ser Ser Arg Ser Asp Gln
        130                 135                 140

AGG CCA TAT TGC TGG CAC TAC CCA CCT CCA CAA TGT ACC ATC GTA CCT     478
Arg Pro Tyr Cys Trp His Tyr Pro Pro Pro Gln Cys Thr Ile Val Pro
    145                 150                 155

GCG TCG GAG GTG TGC GGC CCA GTG TAC TGC TTC ACC CCA AGC CCT GTC     526
Ala Ser Glu Val Cys Gly Pro Val Tyr Cys Phe Thr Pro Ser Pro Val
160                 165                 170                 175

GTC GTG GGG ACG ACC GAT CGT TTC GGT GTC CCT ACG TAT AGA TGG GGG     574
Val Val Gly Thr Thr Asp Arg Phe Gly Val Pro Thr Tyr Arg Trp Gly
                180                 185                 190
```

-continued

GAG AAC GAG ACT GAC GTG CTG CTG CTC AAC AAC ACG CGG CCG CCG CAA 622
Glu Asn Glu Thr Asp Val Leu Leu Leu Asn Asn Thr Arg Pro Pro Gln
195 200 205

GGC AAC TGG TTC GGC TGC ACA TGG ATG AAT AGC ACC GGG TTC ACC AAG 670
Gly Asn Trp Phe Gly Cys Thr Trp Met Asn Ser Thr Gly Phe Thr Lys
210 215 220

ACA TGT GGG GGG CCC CCC TGT AAC ATC GGG GGG GTC GGC AAC AAC ACC 718
Thr Cys Gly Gly Pro Pro Cys Asn Ile Gly Gly Val Gly Asn Asn Thr
225 230 235

CTG ACC TGC CCC ACG GAC TGC TTC CGG AAG CAC CCC GAG GCT ACC TAC 766
Leu Thr Cys Pro Thr Asp Cys Phe Arg Lys His Pro Glu Ala Thr Tyr
240 245 250 255

ACA AAA TGT GGT TCG GGG CCT TGG CTG ACA CCT AGG TGC ATG GTT GAC 814
Thr Lys Cys Gly Ser Gly Pro Trp Leu Thr Pro Arg Cys Met Val Asp
260 265 270

TAT CCA TAC AGG CTC TGG CAT TAC CCC TGC ACT GTT AAC TTT ACC ATC 862
Tyr Pro Tyr Arg Leu Trp His Tyr Pro Cys Thr Val Asn Phe Thr Ile
275 280 285

TTC AAG GTT AGG ATG TAT GTG GGG GGG GTG GAG GAC AGG CTC AAT GCT 910
Phe Lys Val Arg Met Tyr Val Gly Gly Val Glu Asp Arg Leu Asn Ala
290 295 300

GCA TGC AAT TGG ACC CGA GGA GAG CGT TGT GAC TTG GAG GAC AGG GAT 958
Ala Cys Asn Trp Thr Arg Gly Glu Arg Cys Asp Leu Glu Asp Arg Asp
305 310 315

AGG CCG GAG CTC AGC CCG CTG CTG CTG TCT ACA ACA GAG TGG CAG GTA 1006
Arg Pro Glu Leu Ser Pro Leu Leu Leu Ser Thr Thr Glu Trp Gln Val
320 325 330 335

CTG CCC TGT TCC TTC ACC ACC CTA CCA GCT CTG TCC ACT GGC TTG ATT 1054
Leu Pro Cys Ser Phe Thr Thr Leu Pro Ala Leu Ser Thr Gly Leu Ile
340 345 350

CAC CTC CAT CAG AAC ATC GTG GAC GTG CAA TAC CTA TAC GGT ATA GGG 1102
His Leu His Gln Asn Ile Val Asp Val Gln Tyr Leu Tyr Gly Ile Gly
355 360 365

TCA GCG GTT GTC TCC TTT GCA ATC AAA TGG GAG TAT GTC CTG TTG CTT 1150
Ser Ala Val Val Ser Phe Ala Ile Lys Trp Glu Tyr Val Leu Leu Leu
370 375 380

TTC CTT CTC CTA GCG GAC GCA CGT GTC TGT GCC TGC TTG TGG ATG ATG 1198
Phe Leu Leu Leu Ala Asp Ala Arg Val Cys Ala Cys Leu Trp Met Met
385 390 395

CTG CTG ATA 1207
Leu Leu Ile
400

( 2 ) INFORMATION FOR SEQ ID NO:7:

( i ) SEQUENCE CHARACTERISTICS:
( A ) LENGTH: 402 amino acids
( B ) TYPE: amino acid
( D ) TOPOLOGY: linear ( i i ) MOLECULE TYPE: protein ( x i ) SEQUENCE DESCRIPTION: SEQ ID NO:7:

Ile Pro Gln Ala Val Val Asp Met Val Ala Gly Ala His Trp Gly Val
1 5 10 15

Leu Ala Gly Leu Ala Tyr Tyr Ser Met Ala Gly Asn Trp Ala Lys Val
20 25 30

Leu Ile Val Met Leu Leu Phe Ala Gly Val Asp Gly Asp Thr His Val
35 40 45

Thr Gly Gly Ala Gln Ala Lys Thr Thr Asn Arg Leu Val Ser Met Phe
50 55 60

-continued

Ala Ser Gly Pro Ser Gln Lys Ile Gln Leu Ile Asn Thr Asn Gly Ser
65 70 75 80

Trp His Ile Asn Arg Thr Ala Leu Asn Cys Asn Asp Ser Leu Gln Thr
85 90 95

Gly Phe Leu Ala Ala Leu Phe Tyr Thr His Ser Phe Asn Ser Ser Gly
100 105 110

Cys Pro Glu Arg Met Ala Gln Cys Arg Thr Ile Asp Lys Phe Asp Gln
115 120 125

Gly Trp Gly Pro Ile Thr Tyr Ala Glu Ser Ser Arg Ser Asp Gln Arg
130 135 140

Pro Tyr Cys Trp His Tyr Pro Pro Pro Gln Cys Thr Ile Val Pro Ala
145 150 155 160

Ser Glu Val Cys Gly Pro Val Tyr Cys Phe Thr Pro Ser Pro Val Val
165 170 175

Val Gly Thr Thr Asp Arg Phe Gly Val Pro Thr Tyr Arg Trp Gly Glu
180 185 190

Asn Glu Thr Asp Val Leu Leu Leu Asn Asn Thr Arg Pro Pro Gln Gly
195 200 205

Asn Trp Phe Gly Cys Thr Trp Met Asn Ser Thr Gly Phe Thr Lys Thr
210 215 220

Cys Gly Gly Pro Pro Cys Asn Ile Gly Gly Val Gly Asn Asn Thr Leu
225 230 235 240

Thr Cys Pro Thr Asp Cys Phe Arg Lys His Pro Glu Ala Thr Tyr Thr
245 250 255

Lys Cys Gly Ser Gly Pro Trp Leu Thr Pro Arg Cys Met Val Asp Tyr
260 265 270

Pro Tyr Arg Leu Trp His Tyr Pro Cys Thr Val Asn Phe Thr Ile Phe
275 280 285

Lys Val Arg Met Tyr Val Gly Gly Val Glu Asp Arg Leu Asn Ala Ala
290 295 300

Cys Asn Trp Thr Arg Gly Glu Arg Cys Asp Leu Glu Asp Arg Asp Arg
305 310 315 320

Pro Glu Leu Ser Pro Leu Leu Leu Ser Thr Thr Glu Trp Gln Val Leu
325 330 335

Pro Cys Ser Phe Thr Thr Leu Pro Ala Leu Ser Thr Gly Leu Ile His
340 345 350

Leu His Gln Asn Ile Val Asp Val Gln Tyr Leu Tyr Gly Ile Gly Ser
355 360 365

Ala Val Val Ser Phe Ala Ile Lys Trp Glu Tyr Val Leu Leu Leu Phe
370 375 380

Leu Leu Leu Ala Asp Ala Arg Val Cys Ala Cys Leu Trp Met Met Leu
385 390 395 400

Leu Ile ( 2 ) INFORMATION FOR SEQ ID NO:8:

( i ) SEQUENCE CHARACTERISTICS:
( A ) LENGTH: 1207 base pairs
( B ) TYPE: nucleic acid
( C ) STRANDEDNESS: double
( D ) TOPOLOGY: linear ( i i ) MOLECULE TYPE: DNA (genomic)

( i v ) ANTI-SENSE: NO ( v i ) ORIGINAL SOURCE:
( A ) ORGANISM: Hepatitis C virus ( v i i ) IMMEDIATE SOURCE:
( B ) CLONE: HCV-J ( i x ) FEATURE:
( A ) NAME/KEY: CDS
( B ) LOCATION: 2..1207

( x i ) SEQUENCE DESCRIPTION: SEQ ID NO:8:

```
G ATC CCA CAA GCC GTC GTG GAC ATG GTG GCG GGG GCC CAC TGG GGT      46
  Ile Pro Gln Ala Val Val Asp Met Val Ala Gly Ala His Trp Gly
   1               5                  10                  15

GTC CTA GCG GGC CTT GCC TAC TAT TCC ATG GTG GGG AAC TGG GCT AAG    94
Val Leu Ala Gly Leu Ala Tyr Tyr Ser Met Val Gly Asn Trp Ala Lys
                 20                  25                  30

GTC TTG ATT GTG ATG CTA CTC TTT GCT GGC GTT GAC GGG CAC ACC CAC   142
Val Leu Ile Val Met Leu Leu Phe Ala Gly Val Asp Gly His Thr His
             35                  40                  45

GTG ACA GGG GGA AGG GTA GCC TCC AGC ACC CAG AGC CTC GTG TCC TGG   190
Val Thr Gly Gly Arg Val Ala Ser Ser Thr Gln Ser Leu Val Ser Trp
         50                  55                  60

CTC TCA CAA GGC CCA TCT CAG AAA ATC CAA CTC GTG AAC ACC AAC GGC   238
Leu Ser Gln Gly Pro Ser Gln Lys Ile Gln Leu Val Asn Thr Asn Gly
     65                  70                  75

AGC TGG CAC ATC AAC AGG ACC GCT CTG AAT TGC AAT GAC TCC CTC CAA   286
Ser Trp His Ile Asn Arg Thr Ala Leu Asn Cys Asn Asp Ser Leu Gln
 80                  85                  90                  95

ACT GGG TTC ATT GCT GCG CTG TTC TAC GCA CAC AGG TTC AAC GCG TCC   334
Thr Gly Phe Ile Ala Ala Leu Phe Tyr Ala His Arg Phe Asn Ala Ser
                100                 105                 110

GGG TGC CCA GAG CGC ATG GCT AGC TGC CGC CCC ATC GAT GAG TTC GCT   382
Gly Cys Pro Glu Arg Met Ala Ser Cys Arg Pro Ile Asp Glu Phe Ala
            115                 120                 125

CAG GGG TGG GGT CCC ATC ACT CAT GAT ATG CCT GAG AGC TCG GAC CAG   430
Gln Gly Trp Gly Pro Ile Thr His Asp Met Pro Glu Ser Ser Asp Gln
        130                 135                 140

AGG CCA TAT TGC TGG CAC TAC GCG CCT CGA CCG TGC GGG ATC GTG CCT   478
Arg Pro Tyr Cys Trp His Tyr Ala Pro Arg Pro Cys Gly Ile Val Pro
    145                 150                 155

GCG TCG CAG GTG TGT GGT CCA GTG TAT TGC TTC ACT CCG AGC CCT GTT   526
Ala Ser Gln Val Cys Gly Pro Val Tyr Cys Phe Thr Pro Ser Pro Val
160                 165                 170                 175

GTA GTG GGG ACG ACC GAT CGT TTC GGC GCT CCT ACG TAT AGC TGG GGG   574
Val Val Gly Thr Thr Asp Arg Phe Gly Ala Pro Thr Tyr Ser Trp Gly
                180                 185                 190

GAG AAT GAG ACA GAC GTG CTG CTA CTT AGC AAC ACG CGG CCG CCT CAA   622
Glu Asn Glu Thr Asp Val Leu Leu Leu Ser Asn Thr Arg Pro Pro Gln
            195                 200                 205

GGC AAC TGG TTT GGG TGC ACG TGG ATG AAC AGC ACT GGG TTC ACC AAG   670
Gly Asn Trp Phe Gly Cys Thr Trp Met Asn Ser Thr Gly Phe Thr Lys
        210                 215                 220

ACG TGC GGG GGC CCT CCG TGC AAC ATC GGG GGG GTC GGC AAC AAC ACC   718
Thr Cys Gly Gly Pro Pro Cys Asn Ile Gly Gly Val Gly Asn Asn Thr
    225                 230                 235

TTG GTC TGC CCC ACG GAT TGC TTC CGG AAG CAC CCC GAG GCC ACT TAC   766
Leu Val Cys Pro Thr Asp Cys Phe Arg Lys His Pro Glu Ala Thr Tyr
240                 245                 250                 255

ACA AAG TGT GGC TCG GGG CCC TGG TTG ACA CCC AGG TGC ATG GTT GAC   814
Thr Lys Cys Gly Ser Gly Pro Trp Leu Thr Pro Arg Cys Met Val Asp
                260                 265                 270

TAC CCA TAC AGG CTC TGG CAC TAC CCC TGC ACT GTT AAC TTT ACC GTC   862
Tyr Pro Tyr Arg Leu Trp His Tyr Pro Cys Thr Val Asn Phe Thr Val
```

-continued

```
                    275                             280                             285

TTT AAG GTC AGG ATG TAT GTG GGG GGC GTG GAG CAC AGG CTC AAT GCT     910
Phe Lys Val Arg Met Tyr Val Gly Gly Val Glu His Arg Leu Asn Ala
        290                     295                     300

GCA TGC AAT TGG ACT CGA GGA GAG CGC TGT GAC TTG GAG GAC AGG GAT     958
Ala Cys Asn Trp Thr Arg Gly Glu Arg Cys Asp Leu Glu Asp Arg Asp
    305                     310                     315

AGG TCA GAA CTC AGC CCG CTG CTG CTG TCT ACA ACA GAG TGG CAG ATA    1006
Arg Ser Glu Leu Ser Pro Leu Leu Leu Ser Thr Thr Glu Trp Gln Ile
320                     325                     330                     335

CTG CCC TGT TCC TTC ACC ACC CTA CCG GCC CTG TCC ACT GGC TTG ATC    1054
Leu Pro Cys Ser Phe Thr Thr Leu Pro Ala Leu Ser Thr Gly Leu Ile
                340                     345                     350

CAT CTT CAC CGG AAC ATC GTG GAC GTG CAA TAC CTG TAC GGT ATA GGG    1102
His Leu His Arg Asn Ile Val Asp Val Gln Tyr Leu Tyr Gly Ile Gly
            355                     360                     365

TCG GCA GTT GTC TCC TTT GCA ATC AAA TGG GAG TAT ATC CTG TTG CTT    1150
Ser Ala Val Val Ser Phe Ala Ile Lys Trp Glu Tyr Ile Leu Leu Leu
        370                     375                     380

TTC CTT CTT CTG GCG GAC GCG CGC GTC TGT GCC TGC TTG TGG ATG ATG    1198
Phe Leu Leu Leu Ala Asp Ala Arg Val Cys Ala Cys Leu Trp Met Met
    385                     390                     395

CTG CTG ATA                                                        1207
Leu Leu Ile
400
```

( 2 ) INFORMATION FOR SEQ ID NO:9:

( i ) SEQUENCE CHARACTERISTICS:
( A ) LENGTH: 402 amino acids
( B ) TYPE: amino acid
( D ) TOPOLOGY: linear ( i i ) MOLECULE TYPE: protein ( x i ) SEQUENCE DESCRIPTION: SEQ ID NO:9:

```
Ile Pro Gln Ala Val Val Asp Met Val Ala Gly Ala His Trp Gly Val
1               5                   10                  15

Leu Ala Gly Leu Ala Tyr Tyr Ser Met Val Gly Asn Trp Ala Lys Val
            20                  25                  30

Leu Ile Val Met Leu Leu Phe Ala Gly Val Asp Gly His Thr His Val
        35                  40                  45

Thr Gly Gly Arg Val Ala Ser Ser Thr Gln Ser Leu Val Ser Trp Leu
    50                  55                  60

Ser Gln Gly Pro Ser Gln Lys Ile Gln Leu Val Asn Thr Asn Gly Ser
65                  70                  75                  80

Trp His Ile Asn Arg Thr Ala Leu Asn Cys Asn Asp Ser Leu Gln Thr
                85                  90                  95

Gly Phe Ile Ala Ala Leu Phe Tyr Ala His Arg Phe Asn Ala Ser Gly
            100                 105                 110

Cys Pro Glu Arg Met Ala Ser Cys Arg Pro Ile Asp Glu Phe Ala Gln
        115                 120                 125

Gly Trp Gly Pro Ile Thr His Asp Met Pro Glu Ser Ser Asp Gln Arg
    130                 135                 140

Pro Tyr Cys Trp His Tyr Ala Pro Arg Pro Cys Gly Ile Val Pro Ala
145                 150                 155                 160

Ser Gln Val Cys Gly Pro Val Tyr Cys Phe Thr Pro Ser Pro Val Val
                165                 170                 175

Val Gly Thr Thr Asp Arg Phe Gly Ala Pro Thr Tyr Ser Trp Gly Glu
```

-continued

```
                    180                                                 185                                          190

Asn Glu Thr Asp Val Leu Leu Leu Ser Asn Thr Arg Pro Pro Gln Gly
        195                     200                     205

Asn Trp Phe Gly Cys Thr Trp Met Asn Ser Thr Gly Phe Thr Lys Thr
    210                 215                     220

Cys Gly Gly Pro Pro Cys Asn Ile Gly Gly Val Gly Asn Asn Thr Leu
225                 230                     235                 240

Val Cys Pro Thr Asp Cys Phe Arg Lys His Pro Glu Ala Thr Tyr Thr
                245                     250                     255

Lys Cys Gly Ser Gly Pro Trp Leu Thr Pro Arg Cys Met Val Asp Tyr
            260                     265                     270

Pro Tyr Arg Leu Trp His Tyr Pro Cys Thr Val Asn Phe Thr Val Phe
        275                     280                     285

Lys Val Arg Met Tyr Val Gly Gly Val Glu His Arg Leu Asn Ala Ala
    290                     295                     300

Cys Asn Trp Thr Arg Gly Glu Arg Cys Asp Leu Glu Asp Arg Asp Arg
305                 310                     315                 320

Ser Glu Leu Ser Pro Leu Leu Leu Ser Thr Thr Glu Trp Gln Ile Leu
                325                     330                     335

Pro Cys Ser Phe Thr Thr Leu Pro Ala Leu Ser Thr Gly Leu Ile His
            340                     345                     350

Leu His Arg Asn Ile Val Asp Val Gln Tyr Leu Tyr Gly Ile Gly Ser
        355                     360                     365

Ala Val Val Ser Phe Ala Ile Lys Trp Glu Tyr Ile Leu Leu Leu Phe
    370                     375                     380

Leu Leu Leu Ala Asp Ala Arg Val Cys Ala Cys Leu Trp Met Met Leu
385                 390                     395                 400

Leu Ile
```

( 2 ) INFORMATION FOR SEQ ID NO:10:

( i ) SEQUENCE CHARACTERISTICS:
( A ) LENGTH: 1207 base pairs
( B ) TYPE: nucleic acid
( C ) STRANDEDNESS: double
( D ) TOPOLOGY: linear ( i i ) MOLECULE TYPE: DNA (genomic)

( i v ) ANTI-SENSE: NO ( v i ) ORIGINAL SOURCE:
( A ) ORGANISM: Hepatitis C virus ( v i i ) IMMEDIATE SOURCE:
( B ) CLONE: HCV-RNA33

( i x ) FEATURE:
( A ) NAME/KEY: CDS
( B ) LOCATION: 2..1207

( x i ) SEQUENCE DESCRIPTION: SEQ ID NO:10:

```
G ATC CCG CAA GCT GTC GTG GAC ATG GTG GCG GGG GCC CAC TGG GGA     46
  Ile Pro Gln Ala Val Val Asp Met Val Ala Gly Ala His Trp Gly
   1               5                  10                  15

GTC CTG GCG GGC CTG GCC TAC TAT TCC ATG GTG GGG AAC TGG GCT AAG     94
Val Leu Ala Gly Leu Ala Tyr Tyr Ser Met Val Gly Asn Trp Ala Lys
                20                  25                  30

GTT TTG ATT GTG ATG CTA CTC TTT GCC GGC GTT GAC GGG CAA ACC TAT    142
Val Leu Ile Val Met Leu Leu Phe Ala Gly Val Asp Gly Gln Thr Tyr
            35                  40                  45
```

-continued

```
ACG ACG GGG GGG GCG GTT GCC CGC ACC ACC ACC GGG TTC GCG TCC CTC      190
Thr Thr Gly Gly Ala Val Ala Arg Thr Thr Thr Gly Phe Ala Ser Leu
        50                  55                  60

TTC TCC GCT GGG TCG CAG GAG AAC ATC CAG CTT ATA AAC ACC AAT GGC      238
Phe Ser Ala Gly Ser Gln Glu Asn Ile Gln Leu Ile Asn Thr Asn Gly
    65                  70                  75

AGC TGG CAC ATC AAC AGG ACT GCC CTG AAC TGC AAC GAC TCC CTC AAC      286
Ser Trp His Ile Asn Arg Thr Ala Leu Asn Cys Asn Asp Ser Leu Asn
80                  85                  90                  95

ACT GGA TTT CTT GCC GCG CTG TTC TAC ACA CAC AAG TTC AAC TCA TCC      334
Thr Gly Phe Leu Ala Ala Leu Phe Tyr Thr His Lys Phe Asn Ser Ser
                100                 105                 110

AGA GCC GAG AGC GTA TTG GCC AGC TGC CGC TTC ATC GAC GAG TTC GAT      382
Arg Ala Glu Ser Val Leu Ala Ser Cys Arg Phe Ile Asp Glu Phe Asp
            115                 120                 125

CAG GGA TGG GGC CCC ATC ACT TAC ACC GAG CGT AAC AGT TCG GAC CAG      430
Gln Gly Trp Gly Pro Ile Thr Tyr Thr Glu Arg Asn Ser Ser Asp Gln
        130                 135                 140

AGG CCT TAT TGC TGG CAC TAT CCA CCC CGA CAG TGT GGT ATC ATA CCC      478
Arg Pro Tyr Cys Trp His Tyr Pro Pro Arg Gln Cys Gly Ile Ile Pro
    145                 150                 155

GCG TCG GAG GTG TGC GGT CCA GTG TAT TGT TTC ACC CCA AGC CCT GTT      526
Ala Ser Glu Val Cys Gly Pro Val Tyr Cys Phe Thr Pro Ser Pro Val
160                 165                 170                 175

GTG GTG GGG ACA ACC GAT CGG TTC GGT GTC CCT ACA TAC AGC TGG GGG      574
Val Val Gly Thr Thr Asp Arg Phe Gly Val Pro Thr Tyr Ser Trp Gly
                180                 185                 190

GAG AAT GAG ACG GAC GTG CTG GTT CTC AAC AAC ACG CGG CCG CCG CAG      622
Glu Asn Glu Thr Asp Val Leu Val Leu Asn Asn Thr Arg Pro Pro Gln
            195                 200                 205

GGC AAC TGG TTC GGC TGT ACA TGG ATG AAT GGC ACT GGT TTC ACC AAG      670
Gly Asn Trp Phe Gly Cys Thr Trp Met Asn Gly Thr Gly Phe Thr Lys
        210                 215                 220

ACA TGC GGG GGT CCC CCG TGT CAC ATC GGG GGG CGC GGC AAC AAC ACC      718
Thr Cys Gly Gly Pro Pro Cys His Ile Gly Gly Arg Gly Asn Asn Thr
    225                 230                 235

CTG ACT TGC CCC ACG GAC TGC TTC CGG AAG CAT CCC GAG GCT ACG TAT      766
Leu Thr Cys Pro Thr Asp Cys Phe Arg Lys His Pro Glu Ala Thr Tyr
240                 245                 250                 255

ACA AAA TGT GGT TCG GGG CCT TGG TTG ACA CCT AGG TGC ATG GTT GAT      814
Thr Lys Cys Gly Ser Gly Pro Trp Leu Thr Pro Arg Cys Met Val Asp
                260                 265                 270

TAC CCA TAC AGG CTC TGG CAC TAC CCC TGC ACT GTC AAC TTT ACC ACC      862
Tyr Pro Tyr Arg Leu Trp His Tyr Pro Cys Thr Val Asn Phe Thr Thr
            275                 280                 285

TTT AAG GTT AGG ATG TAT GTG GGG GGC GTG GAG CAC AGG CTC ATT GCT      910
Phe Lys Val Arg Met Tyr Val Gly Gly Val Glu His Arg Leu Ile Ala
        290                 295                 300

GCA TGC AAT TGG ACT CGA GGA GAC CGT TGT AAC TTG GAG GAC AGG GAT      958
Ala Cys Asn Trp Thr Arg Gly Asp Arg Cys Asn Leu Glu Asp Arg Asp
    305                 310                 315

AGA TCA GAG CTT AGT CCG CTG CTG CTG TCT ACG ACA GAG TGG CAG ATA     1006
Arg Ser Glu Leu Ser Pro Leu Leu Leu Ser Thr Thr Glu Trp Gln Ile
320                 325                 330                 335

CTG CCC TGT TCC TTC ACC ACC CTA CCG GCT CTC TCC ACC GGT TTG ATC     1054
Leu Pro Cys Ser Phe Thr Thr Leu Pro Ala Leu Ser Thr Gly Leu Ile
                340                 345                 350

CAT CTC CAT CAG AAC ATC GTG GAC GTG CAA TAC CTG TAC GGT ATA GGG     1102
His Leu His Gln Asn Ile Val Asp Val Gln Tyr Leu Tyr Gly Ile Gly
            355                 360                 365
```

-continued

```
TCT GCT GTT GTC TCC ATT GCA ATC AGG TGG GAA TAT GTC CTG TTG CTT      1150
Ser Ala Val Val Ser Ile Ala Ile Arg Trp Glu Tyr Val Leu Leu Leu
        370                 375                 380

TTC CTT CTC CTG GCG GAC GCG CGT GTC TGT GCC TGC TTG TGG ATG ATG      1198
Phe Leu Leu Leu Ala Asp Ala Arg Val Cys Ala Cys Leu Trp Met Met
    385                     390                 395

CTG CTG ATA                                                          1207
Leu Leu Ile
400
```

( 2 ) INFORMATION FOR SEQ ID NO:11:

( i ) SEQUENCE CHARACTERISTICS:
( A ) LENGTH: 402 amino acids
( B ) TYPE: amino acid
( D ) TOPOLOGY: linear ( i i ) MOLECULE TYPE: protein ( x i ) SEQUENCE DESCRIPTION: SEQ ID NO:11:

```
Ile Pro Gln Ala Val Val Asp Met Val Ala Gly Ala His Trp Gly Val
  1             5                  10                  15

Leu Ala Gly Leu Ala Tyr Tyr Ser Met Val Gly Asn Trp Ala Lys Val
             20                  25                  30

Leu Ile Val Met Leu Leu Phe Ala Gly Val Asp Gly Gln Thr Tyr Thr
         35                  40                  45

Thr Gly Gly Ala Val Ala Arg Thr Thr Thr Gly Phe Ala Ser Leu Phe
     50                  55                  60

Ser Ala Gly Ser Gln Glu Asn Ile Gln Leu Ile Asn Thr Asn Gly Ser
 65                  70                  75                  80

Trp His Ile Asn Arg Thr Ala Leu Asn Cys Asn Asp Ser Leu Asn Thr
                 85                  90                  95

Gly Phe Leu Ala Ala Leu Phe Tyr Thr His Lys Phe Asn Ser Ser Arg
            100                 105                 110

Ala Glu Ser Val Leu Ala Ser Cys Arg Phe Ile Asp Glu Phe Asp Gln
        115                 120                 125

Gly Trp Gly Pro Ile Thr Tyr Thr Glu Arg Asn Ser Ser Asp Gln Arg
    130                 135                 140

Pro Tyr Cys Trp His Tyr Pro Pro Arg Gln Cys Gly Ile Ile Pro Ala
145                 150                 155                 160

Ser Glu Val Cys Gly Pro Val Tyr Cys Phe Thr Pro Ser Pro Val Val
                165                 170                 175

Val Gly Thr Thr Asp Arg Phe Gly Val Pro Thr Tyr Ser Trp Gly Glu
            180                 185                 190

Asn Glu Thr Asp Val Leu Val Leu Asn Asn Thr Arg Pro Pro Gln Gly
        195                 200                 205

Asn Trp Phe Gly Cys Thr Trp Met Asn Gly Thr Gly Phe Thr Lys Thr
    210                 215                 220

Cys Gly Gly Pro Pro Cys His Ile Gly Gly Arg Gly Asn Asn Thr Leu
225                 230                 235                 240

Thr Cys Pro Thr Asp Cys Phe Arg Lys His Pro Glu Ala Thr Tyr Thr
                245                 250                 255

Lys Cys Gly Ser Gly Pro Trp Leu Thr Pro Arg Cys Met Val Asp Tyr
            260                 265                 270

Pro Tyr Arg Leu Trp His Tyr Pro Cys Thr Val Asn Phe Thr Thr Phe
        275                 280                 285

Lys Val Arg Met Tyr Val Gly Gly Val Glu His Arg Leu Ile Ala Ala
    290                 295                 300
```

```
Cys Asn Trp Thr Arg Gly Asp Arg Cys Asn Leu Glu Asp Arg Asp Arg
305                 310                 315                 320

Ser Glu Leu Ser Pro Leu Leu Leu Ser Thr Thr Glu Trp Gln Ile Leu
                325                 330                 335

Pro Cys Ser Phe Thr Thr Leu Pro Ala Leu Ser Thr Gly Leu Ile His
            340                 345                 350

Leu His Gln Asn Ile Val Asp Val Gln Tyr Leu Tyr Gly Ile Gly Ser
        355                 360                 365

Ala Val Val Ser Ile Ala Ile Arg Trp Glu Tyr Val Leu Leu Leu Phe
    370                 375                 380

Leu Leu Leu Ala Asp Ala Arg Val Cys Ala Cys Leu Trp Met Met Leu
385                 390                 395                 400

Leu Ile
```

( 2 ) INFORMATION FOR SEQ ID NO:12:

( i ) SEQUENCE CHARACTERISTICS:
( A ) LENGTH: 1207 base pairs
( B ) TYPE: nucleic acid
( C ) STRANDEDNESS: double
( D ) TOPOLOGY: linear ( i i ) MOLECULE TYPE: DNA (genomic)

( i v ) ANTI-SENSE: NO ( v i ) ORIGINAL SOURCE:
( A ) ORGANISM: Hepatitis C virus ( v i i ) IMMEDIATE SOURCE:
( B ) CLONE: HCV1

( i x ) FEATURE:
( A ) NAME/KEY: CDS
( B ) LOCATION: 2..1207

( x i ) SEQUENCE DESCRIPTION: SEQ ID NO:12:

```
G ATC CCA CAA GCC ATC TTG GAC ATG ATC GCT GGT GCT CAC TGG GGA        46
  Ile Pro Gln Ala Ile Leu Asp Met Ile Ala Gly Ala His Trp Gly
    1               5                  10                  15

GTC CTG GCG GGC ATA GCG TAT TTC TCC ATG GTG GGG AAC TGG GCG AAG      94
Val Leu Ala Gly Ile Ala Tyr Phe Ser Met Val Gly Asn Trp Ala Lys
                 20                  25                  30

GTC CTG GTA GTG CTG CTG CTA TTT GCC GGC GTC GAC GCG GAA ACC CAC     142
Val Leu Val Val Leu Leu Leu Phe Ala Gly Val Asp Ala Glu Thr His
             35                  40                  45

GTC ACC GGG GGA AGT GCC GGC CAC ACT GTG TCT GGA TTT GTT AGC CTC     190
Val Thr Gly Gly Ser Ala Gly His Thr Val Ser Gly Phe Val Ser Leu
         50                  55                  60

CTC GCA CCA GGC GCC AAG CAG AAC GTC CAG CTG ATC AAC ACC AAC GGC     238
Leu Ala Pro Gly Ala Lys Gln Asn Val Gln Leu Ile Asn Thr Asn Gly
     65                  70                  75

AGT TGG CAC CTC AAT AGC ACG GCC CTG AAC TGC AAT GAT AGC CTC AAC     286
Ser Trp His Leu Asn Ser Thr Ala Leu Asn Cys Asn Asp Ser Leu Asn
 80                  85                  90                  95

ACC GGC TGG TTG GCA GGG CTT TTC TAT CAC CAC AAG TTC AAC TCT TCA     334
Thr Gly Trp Leu Ala Gly Leu Phe Tyr His His Lys Phe Asn Ser Ser
                100                 105                 110

GGC TGT CCT GAG AGG CTA GCC AGC TGC CGA CCC CTT ACC GAT TTT GAC     382
Gly Cys Pro Glu Arg Leu Ala Ser Cys Arg Pro Leu Thr Asp Phe Asp
            115                 120                 125

CAG GGC TGG GGC CCT ATC AGT TAT GCC AAC GGA AGC GGC CCC GAC CAG     430
Gln Gly Trp Gly Pro Ile Ser Tyr Ala Asn Gly Ser Gly Pro Asp Gln
```

-continued 130 135 140

CGC CCC TAC TGC TGG CAC TAC CCC CCA AAA CCT TGC GGT ATT GTG CCC 478
Arg Pro Tyr Cys Trp His Tyr Pro Pro Lys Pro Cys Gly Ile Val Pro
145 150 155

GCG AAG AGT GTG TGT GGT CCG GTA TAT TGC TTC ACT CCC AGC CCC GTG 526
Ala Lys Ser Val Cys Gly Pro Val Tyr Cys Phe Thr Pro Ser Pro Val
160 165 170 175

GTG GTG GGA ACG ACC GAC AGG TCG GGC GCG CCC ACC TAC AGC TGG GGT 574
Val Val Gly Thr Thr Asp Arg Ser Gly Ala Pro Thr Tyr Ser Trp Gly
180 185 190

GAA AAT GAT ACG GAC GTC TTC GTC CTT AAC AAT ACC AGG CCA CCG CTG 622
Glu Asn Asp Thr Asp Val Phe Val Leu Asn Asn Thr Arg Pro Pro Leu
195 200 205

GGC AAT TGG TTC GGT TGT ACC TGG ATG AAC TCA ACT GGA TTC ACC AAA 670
Gly Asn Trp Phe Gly Cys Thr Trp Met Asn Ser Thr Gly Phe Thr Lys
210 215 220

GTG TGC GGA GCG CCT CCT TGT GTC ATC GGA GGG GCG GGC AAC AAC ACC 718
Val Cys Gly Ala Pro Pro Cys Val Ile Gly Gly Ala Gly Asn Asn Thr
225 230 235

CTG CAC TGC CCC ACT GAT TGC TTC CGC AAG CAT CCG GAC GCC ACA TAC 766
Leu His Cys Pro Thr Asp Cys Phe Arg Lys His Pro Asp Ala Thr Tyr
240 245 250 255

TCT CGG TGC GGC TCC GGT CCC TGG ATC ACA CCC AGG TGC CTG GTC GAC 814
Ser Arg Cys Gly Ser Gly Pro Trp Ile Thr Pro Arg Cys Leu Val Asp
260 265 270

TAC CCG TAT AGG CTT TGG CAT TAT CCT TGT ACC ATC AAC TAC ACC ATA 862
Tyr Pro Tyr Arg Leu Trp His Tyr Pro Cys Thr Ile Asn Tyr Thr Ile
275 280 285

TTT AAA ATC AGG ATG TAC GTG GGA GGG GTC GAA CAC AGG CTG GAA GCT 910
Phe Lys Ile Arg Met Tyr Val Gly Gly Val Glu His Arg Leu Glu Ala
290 295 300

GCC TGC AAC TGG ACG CGG GGC GAA CGT TGC GAT CTG GAA GAC AGG GAC 958
Ala Cys Asn Trp Thr Arg Gly Glu Arg Cys Asp Leu Glu Asp Arg Asp
305 310 315

AGG TCC GAG CTC AGC CCG TTA CTG CTG ACC ACT ACA CAG TGG CAG GTC 1006
Arg Ser Glu Leu Ser Pro Leu Leu Leu Thr Thr Thr Gln Trp Gln Val
320 325 330 335

CTC CCG TGT TCC TTC ACA ACC CTA CCA GCC TTG TCC ACC GGC CTC ATC 1054
Leu Pro Cys Ser Phe Thr Thr Leu Pro Ala Leu Ser Thr Gly Leu Ile
340 345 350

CAC CTC CAC CAG AAC ATT GTG GAC GTG CAG TAC TTG TAC GGG GTG GGG 1102
His Leu His Gln Asn Ile Val Asp Val Gln Tyr Leu Tyr Gly Val Gly
355 360 365

TCA AGC ATC GCG TCC TGG GCC ATT AAG TGG GAG TAC GTC GTT CTC CTG 1150
Ser Ser Ile Ala Ser Trp Ala Ile Lys Trp Glu Tyr Val Val Leu Leu
370 375 380

TTC CTT CTG CTT GCA GAC GCG CGC GTC TGC TCC TGC TTG TGG ATG ATG 1198
Phe Leu Leu Leu Ala Asp Ala Arg Val Cys Ser Cys Leu Trp Met Met
385 390 395

CTA CTC ATA 1207
Leu Leu Ile
400

( 2 ) INFORMATION FOR SEQ ID NO:13:

( i ) SEQUENCE CHARACTERISTICS:
( A ) LENGTH: 402 amino acids
( B ) TYPE: amino acid
( D ) TOPOLOGY: linear ( i i ) MOLECULE TYPE: protein ( x i ) SEQUENCE DESCRIPTION: SEQ ID NO:13:

```
Ile Pro Gln Ala Ile Leu Asp Met Ile Ala Gly Ala His Trp Gly Val
1               5                   10                  15

Leu Ala Gly Ile Ala Tyr Phe Ser Met Val Gly Asn Trp Ala Lys Val
            20                  25                  30

Leu Val Val Leu Leu Leu Phe Ala Gly Val Asp Ala Glu Thr His Val
        35                  40                  45

Thr Gly Gly Ser Ala Gly His Thr Val Ser Gly Phe Val Ser Leu Leu
    50                  55                  60

Ala Pro Gly Ala Lys Gln Asn Val Gln Leu Ile Asn Thr Asn Gly Ser
65                  70                  75                  80

Trp His Leu Asn Ser Thr Ala Leu Asn Cys Asn Asp Ser Leu Asn Thr
                85                  90                  95

Gly Trp Leu Ala Gly Leu Phe Tyr His His Lys Phe Asn Ser Ser Gly
            100                 105                 110

Cys Pro Glu Arg Leu Ala Ser Cys Arg Pro Leu Thr Asp Phe Asp Gln
        115                 120                 125

Gly Trp Gly Pro Ile Ser Tyr Ala Asn Gly Ser Gly Pro Asp Gln Arg
    130                 135                 140

Pro Tyr Cys Trp His Tyr Pro Pro Lys Pro Cys Gly Ile Val Pro Ala
145                 150                 155                 160

Lys Ser Val Cys Gly Pro Val Tyr Cys Phe Thr Pro Ser Pro Val Val
                165                 170                 175

Val Gly Thr Thr Asp Arg Ser Gly Ala Pro Thr Tyr Ser Trp Gly Glu
            180                 185                 190

Asn Asp Thr Asp Val Phe Val Leu Asn Asn Thr Arg Pro Pro Leu Gly
        195                 200                 205

Asn Trp Phe Gly Cys Thr Trp Met Asn Ser Thr Gly Phe Thr Lys Val
    210                 215                 220

Cys Gly Ala Pro Pro Cys Val Ile Gly Gly Ala Gly Asn Asn Thr Leu
225                 230                 235                 240

His Cys Pro Thr Asp Cys Phe Arg Lys His Pro Asp Ala Thr Tyr Ser
                245                 250                 255

Arg Cys Gly Ser Gly Pro Trp Ile Thr Pro Arg Cys Leu Val Asp Tyr
            260                 265                 270

Pro Tyr Arg Leu Trp His Tyr Pro Cys Thr Ile Asn Tyr Thr Ile Phe
        275                 280                 285

Lys Ile Arg Met Tyr Val Gly Gly Val Glu His Arg Leu Glu Ala Ala
    290                 295                 300

Cys Asn Trp Thr Arg Gly Glu Arg Cys Asp Leu Glu Asp Arg Asp Arg
305                 310                 315                 320

Ser Glu Leu Ser Pro Leu Leu Leu Thr Thr Thr Gln Trp Gln Val Leu
                325                 330                 335

Pro Cys Ser Phe Thr Thr Leu Pro Ala Leu Ser Thr Gly Leu Ile His
            340                 345                 350

Leu His Gln Asn Ile Val Asp Val Gln Tyr Leu Tyr Gly Val Gly Ser
        355                 360                 365

Ser Ile Ala Ser Trp Ala Ile Lys Trp Glu Tyr Val Val Leu Leu Phe
    370                 375                 380

Leu Leu Leu Ala Asp Ala Arg Val Cys Ser Cys Leu Trp Met Met Leu
385                 390                 395                 400

Leu Ile
```

( 2 ) INFORMATION FOR SEQ ID NO:14:

( i ) SEQUENCE CHARACTERISTICS:
( A ) LENGTH: 1207 base pairs
( B ) TYPE: nucleic acid
( C ) STRANDEDNESS: double
( D ) TOPOLOGY: linear ( i i ) MOLECULE TYPE: DNA (genomic)

( i v ) ANTI-SENSE: NO ( v i ) ORIGINAL SOURCE:
( A ) ORGANISM: Hepatitis C virus ( v i i ) IMMEDIATE SOURCE:
( B ) CLONE: H77

( i x ) FEATURE:
( A ) NAME/KEY: CDS
( B ) LOCATION: 2..1207

( x i ) SEQUENCE DESCRIPTION: SEQ ID NO:14:

```
G ATC CCA CAA GCC ATC ATG GAC ATG ATC GCT GGT GCT CAC TGG GGA        46
  Ile Pro Gln Ala Ile Met Asp Met Ile Ala Gly Ala His Trp Gly
   1               5                   10                  15

GTC CTG GCG GGC ATA GCG TAT TTC TCC ATG GTG GGG AAC TGG GCG AAG      94
Val Leu Ala Gly Ile Ala Tyr Phe Ser Met Val Gly Asn Trp Ala Lys
                20                  25                  30

GTC CTG GTA GTG CTG CTG CTA TTT GCC GGC GTC GAC GCG GAA ACC CAC     142
Val Leu Val Val Leu Leu Leu Phe Ala Gly Val Asp Ala Glu Thr His
            35                  40                  45

GTC ACC GGG GGA AGT GCC GGC CGC ACC ACG GCT GGG CTT GTT GGT CTC     190
Val Thr Gly Gly Ser Ala Gly Arg Thr Thr Ala Gly Leu Val Gly Leu
        50                  55                  60

CTT ACA CCA GGC GCC AAG CAG AAC ATC CAA CTG ATC AAC ACC AAC GGC     238
Leu Thr Pro Gly Ala Lys Gln Asn Ile Gln Leu Ile Asn Thr Asn Gly
    65                  70                  75

AGT GGC TGG TTA GCA GGG CTC TTC TAT CAC CAC AAA TTC AAC TCT TCA     286
Ser Gly Trp Leu Ala Gly Leu Phe Tyr His His Lys Phe Asn Ser Ser
80                  85                  90                  95

GGC TGT CCT GAG AGG TTG GCC AGC TGC CGA CGC CTT ACC GAT TTT GCC     334
Gly Cys Pro Glu Arg Leu Ala Ser Cys Arg Arg Leu Thr Asp Phe Ala
                100                 105                 110

CAG TGG CAC ATC AAT AGC ACG GCC TTG AAC TGC AAT GAA AGC CTT AAC     382
Gln Trp His Ile Asn Ser Thr Ala Leu Asn Cys Asn Glu Ser Leu Asn
            115                 120                 125

ACC GGC TGG GGT CCT ATC AGT TAT GCC AAC GGA AGC GGC CTC GAC GAA     430
Thr Gly Trp Gly Pro Ile Ser Tyr Ala Asn Gly Ser Gly Leu Asp Glu
        130                 135                 140

CGC CCC TAC TGC TGG CAC TAC CCT CCA AGA CCT TGT GGC ATT GTG CCC     478
Arg Pro Tyr Cys Trp His Tyr Pro Pro Arg Pro Cys Gly Ile Val Pro
    145                 150                 155

GCA AAG AGC GTG TGT GGC CCG GTA TAT TGC TTC ACT CCC AGC CCC GTG     526
Ala Lys Ser Val Cys Gly Pro Val Tyr Cys Phe Thr Pro Ser Pro Val
160                 165                 170                 175

GTG GTG GGA ACG ACC GAC AGG TCG GGC GCG CCT ACC TAC AGC TGG GGT     574
Val Val Gly Thr Thr Asp Arg Ser Gly Ala Pro Thr Tyr Ser Trp Gly
                180                 185                 190

GCA AAT GAT ACG GAT GTC TTC GTC CTT AAC AAC ACC AGG CCA CCG CTG     622
Ala Asn Asp Thr Asp Val Phe Val Leu Asn Asn Thr Arg Pro Pro Leu
            195                 200                 205

GGC AAT TGG TTC GGT TGT ACC TGG ATG AAC TCA ACT GGA TTC ACC AAA     670
Gly Asn Trp Phe Gly Cys Thr Trp Met Asn Ser Thr Gly Phe Thr Lys
        210                 215                 220
```

-continued

```
GTG TGC GGA GCG CCC CCT TGT GTC ATC GGA GGG GTG GGC AAC AAC ACC      718
Val Cys Gly Ala Pro Pro Cys Val Ile Gly Gly Val Gly Asn Asn Thr
    225                 230                 235

TTG CTC TGC CCC ACT GAT TGC TTC CGC AAG CAT CCG GAA GCC ACA TAC      766
Leu Leu Cys Pro Thr Asp Cys Phe Arg Lys His Pro Glu Ala Thr Tyr
240                 245                 250                 255

TCT CGG TGC GGC TCC GGT CCC TGG ATT ACA CCC AGG TGC ATG GTC GAC      814
Ser Arg Cys Gly Ser Gly Pro Trp Ile Thr Pro Arg Cys Met Val Asp
                260                 265                 270

TAC CCG TAT AGG CTT TGG CAC TAT CCT TGT ACC ATC AAT TAC ACC ATA      862
Tyr Pro Tyr Arg Leu Trp His Tyr Pro Cys Thr Ile Asn Tyr Thr Ile
            275                 280                 285

TTC AAA GTC AGG ATG TAC GTG GGA GGG GTC GAG CAC AGG CTG GAA GCG      910
Phe Lys Val Arg Met Tyr Val Gly Gly Val Glu His Arg Leu Glu Ala
        290                 295                 300

GCC TGC AAC TGG ACG CGG GGC GAA CGC TGT GAT CTG GAA GAC AGG GAC      958
Ala Cys Asn Trp Thr Arg Gly Glu Arg Cys Asp Leu Glu Asp Arg Asp
    305                 310                 315

AGG TCC GAG CTC AGC CCA TTG CTG CTG TCC ACC ACA CAG TGG CAG GTC     1006
Arg Ser Glu Leu Ser Pro Leu Leu Leu Ser Thr Thr Gln Trp Gln Val
320                 325                 330                 335

CTT CCG TGT TCT TTC ACG ACC CTG CCA GCC TTG TCC ACC GGC CTC ATC     1054
Leu Pro Cys Ser Phe Thr Thr Leu Pro Ala Leu Ser Thr Gly Leu Ile
                340                 345                 350

CAC CTC CAC CAG AAC ATT GTG GAC GTG CAG TAC TTG TAC GGG GTA GGG     1102
His Leu His Gln Asn Ile Val Asp Val Gln Tyr Leu Tyr Gly Val Gly
            355                 360                 365

TCA AGC ATC GCG TCC TGG GCC ATT AAG TGG GAG TAC GTC GTT CTC CTG     1150
Ser Ser Ile Ala Ser Trp Ala Ile Lys Trp Glu Tyr Val Val Leu Leu
        370                 375                 380

TTC CTT CTG CTT GCA GAC GCG CGC GTC TGC TCC TGC TTG TGG ATG ATG     1198
Phe Leu Leu Leu Ala Asp Ala Arg Val Cys Ser Cys Leu Trp Met Met
    385                 390                 395

TTA CTC ATA                                                         1207
Leu Leu Ile
400
```

( 2 ) INFORMATION FOR SEQ ID NO:15:

( i ) SEQUENCE CHARACTERISTICS:
( A ) LENGTH: 402 amino acids
( B ) TYPE: amino acid
( D ) TOPOLOGY: linear ( i i ) MOLECULE TYPE: protein ( x i ) SEQUENCE DESCRIPTION: SEQ ID NO:15:

```
Ile Pro Gln Ala Ile Met Asp Met Ile Ala Gly Ala His Trp Gly Val
 1               5                  10                  15

Leu Ala Gly Ile Ala Tyr Phe Ser Met Val Gly Asn Trp Ala Lys Val
            20                  25                  30

Leu Val Val Leu Leu Leu Phe Ala Gly Val Asp Ala Glu Thr His Val
        35                  40                  45

Thr Gly Gly Ser Ala Gly Arg Thr Thr Ala Gly Leu Val Gly Leu Leu
    50                  55                  60

Thr Pro Gly Ala Lys Gln Asn Ile Gln Leu Ile Asn Thr Asn Gly Ser
 65                 70                  75                  80

Gly Trp Leu Ala Gly Leu Phe Tyr His His Lys Phe Asn Ser Ser Gly
                85                  90                  95

Cys Pro Glu Arg Leu Ala Ser Cys Arg Arg Leu Thr Asp Phe Ala Gln
           100                 105                 110
```

Trp His Ile Asn Ser Thr Ala Leu Asn Cys Asn Glu Ser Leu Asn Thr
115 120 125

Gly Trp Gly Pro Ile Ser Tyr Ala Asn Gly Ser Gly Leu Asp Glu Arg
130 135 140

Pro Tyr Cys Trp His Tyr Pro Pro Arg Pro Cys Gly Ile Val Pro Ala
145 150 155 160

Lys Ser Val Cys Gly Pro Val Tyr Cys Phe Thr Pro Ser Pro Val Val
165 170 175

Val Gly Thr Thr Asp Arg Ser Gly Ala Pro Thr Tyr Ser Trp Gly Ala
180 185 190

Asn Asp Thr Asp Val Phe Val Leu Asn Asn Thr Arg Pro Pro Leu Gly
195 200 205

Asn Trp Phe Gly Cys Thr Trp Met Asn Ser Thr Gly Phe Thr Lys Val
210 215 220

Cys Gly Ala Pro Pro Cys Val Ile Gly Gly Val Gly Asn Asn Thr Leu
225 230 235 240

Leu Cys Pro Thr Asp Cys Phe Arg Lys His Pro Glu Ala Thr Tyr Ser
245 250 255

Arg Cys Gly Ser Gly Pro Trp Ile Thr Pro Arg Cys Met Val Asp Tyr
260 265 270

Pro Tyr Arg Leu Trp His Tyr Pro Cys Thr Ile Asn Tyr Thr Ile Phe
275 280 285

Lys Val Arg Met Tyr Val Gly Gly Val Glu His Arg Leu Glu Ala Ala
290 295 300

Cys Asn Trp Thr Arg Gly Glu Arg Cys Asp Leu Glu Asp Arg Asp Arg
305 310 315 320

Ser Glu Leu Ser Pro Leu Leu Leu Ser Thr Thr Gln Trp Gln Val Leu
325 330 335

Pro Cys Ser Phe Thr Thr Leu Pro Ala Leu Ser Thr Gly Leu Ile His
340 345 350

Leu His Gln Asn Ile Val Asp Val Gln Tyr Leu Tyr Gly Val Gly Ser
355 360 365

Ser Ile Ala Ser Trp Ala Ile Lys Trp Glu Tyr Val Val Leu Leu Phe
370 375 380

Leu Leu Leu Ala Asp Ala Arg Val Cys Ser Cys Leu Trp Met Met Leu
385 390 395 400

Leu Ile ( 2 ) INFORMATION FOR SEQ ID NO:16:

( i ) SEQUENCE CHARACTERISTICS:
( A ) LENGTH: 1207 base pairs
( B ) TYPE: nucleic acid
( C ) STRANDEDNESS: double
( D ) TOPOLOGY: linear ( i i ) MOLECULE TYPE: DNA (genomic)

( i v ) ANTI-SENSE: NO ( v i ) ORIGINAL SOURCE:
( A ) ORGANISM: Hepatitis C virus ( v i i ) IMMEDIATE SOURCE:
( B ) CLONE: H90

( i x ) FEATURE:
( A ) NAME/KEY: CDS
( B ) LOCATION: 2..1207

( x i ) SEQUENCE DESCRIPTION: SEQ ID NO:16:

```
G ATC CCA CAA GCC ATC ATG GAT ATG ATC GCT GGT GCT CAC TGG GGA       46
  Ile Pro Gln Ala Ile Met Asp Met Ile Ala Gly Ala His Trp Gly
  1               5                   10                  15

GTC CTG GCG GGC ATA GCG TAT TTC TCC ATG GTA GGG AAC TGG GCG AAG     94
Val Leu Ala Gly Ile Ala Tyr Phe Ser Met Val Gly Asn Trp Ala Lys
                20                  25                  30

GTC CTA GTA GTG CTG CTG CTA TTT GCC GGC GTC GAC GCG GAA ACC CAC    142
Val Leu Val Val Leu Leu Leu Phe Ala Gly Val Asp Ala Glu Thr His
            35                  40                  45

GTC ACC GGG GGA AGT GCC GGC CGC TCC GTG CTT GGG ATT GCT AGT TTC    190
Val Thr Gly Gly Ser Ala Gly Arg Ser Val Leu Gly Ile Ala Ser Phe
        50                  55                  60

CTT ACA CGA GGC CCC AAG CAG AAC ATÇ CAG CTG ATC AAA ACC AAC GGC    238
Leu Thr Arg Gly Pro Lys Gln Asn Ile Gln Leu Ile Lys Thr Asn Gly
    65                  70                  75

AGT TGG CAC ATC AAT AGC ACG GCC CTG AAC TGC AAT GAC AGC CTT AAC    286
Ser Trp His Ile Asn Ser Thr Ala Leu Asn Cys Asn Asp Ser Leu Asn
80                  85                  90                  95

GCC GGC TGG ATA GCG GGG CTC TTC TAT CAC CAT GGA TTC AAC TCT TCA    334
Ala Gly Trp Ile Ala Gly Leu Phe Tyr His His Gly Phe Asn Ser Ser
                100                 105                 110

GGC TGT CCT GAG AGG TTG GCC AGC TGC CGA CGC CTT ACC GAT TTT GAC    382
Gly Cys Pro Glu Arg Leu Ala Ser Cys Arg Arg Leu Thr Asp Phe Asp
            115                 120                 125

CAG GGC TGG GGC CCT ATC AGT TAT GCC AAC GGA AGC GGC CCC GAC GAA    430
Gln Gly Trp Gly Pro Ile Ser Tyr Ala Asn Gly Ser Gly Pro Asp Glu
        130                 135                 140

CGT CCC TAC TGC TGG CAC TAC CCC CCA AGA CCT TGT GGC ATT GTG CCC    478
Arg Pro Tyr Cys Trp His Tyr Pro Pro Arg Pro Cys Gly Ile Val Pro
    145                 150                 155

GCA AAG AGC GTG TGT GGC CCG GTA TAC TGC TTC ACT CCC AGC CCC GTG    526
Ala Lys Ser Val Cys Gly Pro Val Tyr Cys Phe Thr Pro Ser Pro Val
160                 165                 170                 175

GTG GTG GGA ACG ACC GAC AGG TCG GGC GCG CCT ACC TAC AAC TGG GGT    574
Val Val Gly Thr Thr Asp Arg Ser Gly Ala Pro Thr Tyr Asn Trp Gly
                180                 185                 190

GAA AAT GAT ACG GAT GTC CTC ATC CTT AAC AAC ACC AGG CCG CCG CTG    622
Glu Asn Asp Thr Asp Val Leu Ile Leu Asn Asn Thr Arg Pro Pro Leu
            195                 200                 205

GGC AAT TGG TTC GGT TGT ACC TGG ATG AAC TCA ACT GGA TTC ACC AAA    670
Gly Asn Trp Phe Gly Cys Thr Trp Met Asn Ser Thr Gly Phe Thr Lys
        210                 215                 220

GTG TGC GGA GCG CCC CCT TGT GTC ATC GGA GGG GTG GGC AAC AAC ACC    718
Val Cys Gly Ala Pro Pro Cys Val Ile Gly Gly Val Gly Asn Asn Thr
    225                 230                 235

TTG CGC TGC CCC ACT GAT TGT TTC CGC AAG CAT CCG GAA GCC ACA TAC    766
Leu Arg Cys Pro Thr Asp Cys Phe Arg Lys His Pro Glu Ala Thr Tyr
240                 245                 250                 255

TCT CGG TGC GGC TCC GGT CCC TGG ATC ACA CCC AGG TGC ATG GTC CAC    814
Ser Arg Cys Gly Ser Gly Pro Trp Ile Thr Pro Arg Cys Met Val His
                260                 265                 270

TAC CCG TAT AGG CTT TGG CAC TAT CCT TGT ACC ATC AAT TAC ACT ATA    862
Tyr Pro Tyr Arg Leu Trp His Tyr Pro Cys Thr Ile Asn Tyr Thr Ile
            275                 280                 285

TTT AAA GTC AGG ATG TAC GTG GGA GGG ATC GAG CAC AGG CTG GAA GCG    910
Phe Lys Val Arg Met Tyr Val Gly Gly Ile Glu His Arg Leu Glu Ala
        290                 295                 300

GCC TGC AAC TGG ACG CGG GGC GAA CGT TGC GAT CTG GAA GAC AGG GAC    958
Ala Cys Asn Trp Thr Arg Gly Glu Arg Cys Asp Leu Glu Asp Arg Asp
```

-continued

```
     305                        310                        315

AGG TCC GAG CTC AGC CCA TTG CTG CTG TCC ACT ACG CAG TGG CAG GTC      1006
Arg Ser Glu Leu Ser Pro Leu Leu Leu Ser Thr Thr Gln Trp Gln Val
320                     325                     330                     335

CTT CCG TGT TCT TTC ACG ACC CTG CCA GCC TTG TCC ACC GGC CTC ATC      1054
Leu Pro Cys Ser Phe Thr Thr Leu Pro Ala Leu Ser Thr Gly Leu Ile
                340                     345                     350

CAC CTC CAC CAG AAC ATT GTG GAC GTG CAG TAC TTG TAC GGG GTA GGG      1102
His Leu His Gln Asn Ile Val Asp Val Gln Tyr Leu Tyr Gly Val Gly
            355                     360                     365

TCA AGC ATC GCG TCC TGG ACC ATC AAG TGG GAG TAC GTC GTT CTC CTG      1150
Ser Ser Ile Ala Ser Trp Thr Ile Lys Trp Glu Tyr Val Val Leu Leu
        370                     375                     380

TTC CTC CTG CTT GCA GAC GCG CGC GTC TGC TCC TGC TTG TGG ATG ATG      1198
Phe Leu Leu Leu Ala Asp Ala Arg Val Cys Ser Cys Leu Trp Met Met
    385                     390                     395

TTA CTC ATA                                                          1207
Leu Leu Ile
400
```

( 2 ) INFORMATION FOR SEQ ID NO:17:

( i ) SEQUENCE CHARACTERISTICS:
( A ) LENGTH: 402 amino acids
( B ) TYPE: amino acid
( D ) TOPOLOGY: linear ( i i ) MOLECULE TYPE: protein ( x i ) SEQUENCE DESCRIPTION: SEQ ID NO:17:

```
Ile Pro Gln Ala Ile Met Asp Met Ile Ala Gly Ala His Trp Gly Val
 1               5                  10                  15

Leu Ala Gly Ile Ala Tyr Phe Ser Met Val Gly Asn Trp Ala Lys Val
            20                  25                  30

Leu Val Val Leu Leu Leu Phe Ala Gly Val Asp Ala Glu Thr His Val
        35                  40                  45

Thr Gly Gly Ser Ala Gly Arg Ser Val Leu Gly Ile Ala Ser Phe Leu
    50                  55                  60

Thr Arg Gly Pro Lys Gln Asn Ile Gln Leu Ile Lys Thr Asn Gly Ser
65                  70                  75                  80

Trp His Ile Asn Ser Thr Ala Leu Asn Cys Asn Asp Ser Leu Asn Ala
                85                  90                  95

Gly Trp Ile Ala Gly Leu Phe Tyr His His Gly Phe Asn Ser Ser Gly
            100                 105                 110

Cys Pro Glu Arg Leu Ala Ser Cys Arg Arg Leu Thr Asp Phe Asp Gln
        115                 120                 125

Gly Trp Gly Pro Ile Ser Tyr Ala Asn Gly Ser Gly Pro Asp Glu Arg
    130                 135                 140

Pro Tyr Cys Trp His Tyr Pro Pro Arg Pro Cys Gly Ile Val Pro Ala
145                 150                 155                 160

Lys Ser Val Cys Gly Pro Val Tyr Cys Phe Thr Pro Ser Pro Val Val
                165                 170                 175

Val Gly Thr Thr Asp Arg Ser Gly Ala Pro Thr Tyr Asn Trp Gly Glu
            180                 185                 190

Asn Asp Thr Asp Val Leu Ile Leu Asn Asn Thr Arg Pro Pro Leu Gly
        195                 200                 205

Asn Trp Phe Gly Cys Thr Trp Met Asn Ser Thr Gly Phe Thr Lys Val
    210                 215                 220
```

-continued

```
Cys Gly Ala Pro Pro Cys Val Ile Gly Gly Val Gly Asn Asn Thr Leu
225                 230                 235                 240

Arg Cys Pro Thr Asp Cys Phe Arg Lys His Pro Glu Ala Thr Tyr Ser
                245                 250                 255

Arg Cys Gly Ser Gly Pro Trp Ile Thr Pro Arg Cys Met Val His Tyr
            260                 265                 270

Pro Tyr Arg Leu Trp His Tyr Pro Cys Thr Ile Asn Tyr Thr Ile Phe
        275                 280                 285

Lys Val Arg Met Tyr Val Gly Gly Ile Glu His Arg Leu Glu Ala Ala
    290                 295                 300

Cys Asn Trp Thr Arg Gly Glu Arg Cys Asp Leu Glu Asp Arg Asp Arg
305                 310                 315                 320

Ser Glu Leu Ser Pro Leu Leu Leu Ser Thr Thr Gln Trp Gln Val Leu
                325                 330                 335

Pro Cys Ser Phe Thr Thr Leu Pro Ala Leu Ser Thr Gly Leu Ile His
            340                 345                 350

Leu His Gln Asn Ile Val Asp Val Gln Tyr Leu Tyr Gly Val Gly Ser
        355                 360                 365

Ser Ile Ala Ser Trp Thr Ile Lys Trp Glu Tyr Val Val Leu Leu Phe
    370                 375                 380

Leu Leu Leu Ala Asp Ala Arg Val Cys Ser Cys Leu Trp Met Met Leu
385                 390                 395                 400

Leu Ile
```

( 2 ) INFORMATION FOR SEQ ID NO:18:

( i ) SEQUENCE CHARACTERISTICS:
( A ) LENGTH: 523 base pairs
( B ) TYPE: nucleic acid
( C ) STRANDEDNESS: double
( D ) TOPOLOGY: linear ( i i ) MOLECULE TYPE: DNA (genomic)

( i v ) ANTI-SENSE: NO ( v i ) ORIGINAL SOURCE:
( A ) ORGANISM: Hepatitis C virus ( v i i ) IMMEDIATE SOURCE:
( B ) CLONE: J1(JM)

( i x ) FEATURE:
( A ) NAME/KEY: CDS
( B ) LOCATION: 2..523

( x i ) SEQUENCE DESCRIPTION: SEQ ID NO:18:

```
G ATC CCA CAA GCC ATC TTG GAT ATG ATC GCT GGT GCT CAC TGG GGA      46
  Ile Pro Gln Ala Ile Leu Asp Met Ile Ala Gly Ala His Trp Gly
  1               5                   10                  15

GTC CTG GCG GGC ATA GCG TAT TTC TCC ATG GTG GGG AAC TGG GCG AAG    94
Val Leu Ala Gly Ile Ala Tyr Phe Ser Met Val Gly Asn Trp Ala Lys
                20                  25                  30

GTC CTG GTA GTG CTG TTG CTG TTT GCC GGC GTC GAC GCG GAA ACC ATC   142
Val Leu Val Val Leu Leu Leu Phe Ala Gly Val Asp Ala Glu Thr Ile
            35                  40                  45

GTC TCC GGG GGA CAA GCC GCC CGC GCC ATG TCT GGA CTT GTT AGT CTC   190
Val Ser Gly Gly Gln Ala Ala Arg Ala Met Ser Gly Leu Val Ser Leu
        50                  55                  60

TTC ACA CCA GGC GCT AAG CAG AAC ATC CAG CTG ATC AAC ACC AAC GGC   238
Phe Thr Pro Gly Ala Lys Gln Asn Ile Gln Leu Ile Asn Thr Asn Gly
    65                  70                  75
```

-continued

```
AGT TGG CAC ATC AAT AGC ACG GCC TTG AAC TGC AAT GAA AGC CTT AAC    286
Ser Trp His Ile Asn Ser Thr Ala Leu Asn Cys Asn Glu Ser Leu Asn
 80                 85                  90                  95

ACC GGC TGG TTA GCA GGG CTT ATC TAT CAA CAC AAA TTC AAC TCT TCG    334
Thr Gly Trp Leu Ala Gly Leu Ile Tyr Gln His Lys Phe Asn Ser Ser
                100                 105                 110

GGC TGT CCC GAG AGG TTG GCC AGC TGC CGA CGC CTT ACC GAT TTT GAC    382
Gly Cys Pro Glu Arg Leu Ala Ser Cys Arg Arg Leu Thr Asp Phe Asp
            115                 120                 125

CAG GGC TGG GGC CCT ATC AGT CAT GCC AAC GGA AGC GGC CCC GAC CAA    430
Gln Gly Trp Gly Pro Ile Ser His Ala Asn Gly Ser Gly Pro Asp Gln
        130                 135                 140

CGC CCC TAT TGT TGG CAC TAC CCC CCA AAA CCT TGC GGT ATC GTG CCC    478
Arg Pro Tyr Cys Trp His Tyr Pro Pro Lys Pro Cys Gly Ile Val Pro
    145                 150                 155

GCA AAG AGC GTA TGT GGC CCG GTA TAT TGC TTC ACT CCC AGC CCC        523
Ala Lys Ser Val Cys Gly Pro Val Tyr Cys Phe Thr Pro Ser Pro
160                 165                 170
```

( 2 ) INFORMATION FOR SEQ ID NO:19:

( i ) SEQUENCE CHARACTERISTICS:
( A ) LENGTH: 174 amino acids
( B ) TYPE: amino acid
( D ) TOPOLOGY: linear ( i i ) MOLECULE TYPE: protein ( x i ) SEQUENCE DESCRIPTION: SEQ ID NO:19:

```
Ile Pro Gln Ala Ile Leu Asp Met Ile Ala Gly Ala His Trp Gly Val
1               5                   10                  15

Leu Ala Gly Ile Ala Tyr Phe Ser Met Val Gly Asn Trp Ala Lys Val
            20                  25                  30

Leu Val Val Leu Leu Leu Phe Ala Gly Val Asp Ala Glu Thr Ile Val
        35                  40                  45

Ser Gly Gly Gln Ala Ala Arg Ala Met Ser Gly Leu Val Ser Leu Phe
    50                  55                  60

Thr Pro Gly Ala Lys Gln Asn Ile Gln Leu Ile Asn Thr Asn Gly Ser
65                  70                  75                  80

Trp His Ile Asn Ser Thr Ala Leu Asn Cys Asn Glu Ser Leu Asn Thr
                85                  90                  95

Gly Trp Leu Ala Gly Leu Ile Tyr Gln His Lys Phe Asn Ser Ser Gly
            100                 105                 110

Cys Pro Glu Arg Leu Ala Ser Cys Arg Arg Leu Thr Asp Phe Asp Gln
        115                 120                 125

Gly Trp Gly Pro Ile Ser His Ala Asn Gly Ser Gly Pro Asp Gln Arg
    130                 135                 140

Pro Tyr Cys Trp His Tyr Pro Pro Lys Pro Cys Gly Ile Val Pro Ala
145                 150                 155                 160

Lys Ser Val Cys Gly Pro Val Tyr Cys Phe Thr Pro Ser Pro
                165                 170
```

( 2 ) INFORMATION FOR SEQ ID NO:20:

( i ) SEQUENCE CHARACTERISTICS:
( A ) LENGTH: 523 base pairs
( B ) TYPE: nucleic acid
( C ) STRANDEDNESS: double
( D ) TOPOLOGY: linear ( i i ) MOLECULE TYPE: DNA (genomic)

( i v ) ANTI-SENSE: NO ( v i ) ORIGINAL SOURCE:
( A ) ORGANISM: Hepatitis C virus ( v i i ) IMMEDIATE SOURCE:
( B ) CLONE: J4(JM)

( i x ) FEATURE:
( A ) NAME/KEY: CDS
( B ) LOCATION: 2..523

( x i ) SEQUENCE DESCRIPTION: SEQ ID NO:20:

```
G ATC CCA CAA GCT GTC GTG GAC ATG GTG GCG GGG GCC CAC TGG GGA        46
  Ile Pro Gln Ala Val Val Asp Met Val Ala Gly Ala His Trp Gly
   1               5                  10                  15

GTC CTG GCG GGC CTT GCC TAC TAT TCC ATG GTA GGG AAC TGG GCT AAG      94
Val Leu Ala Gly Leu Ala Tyr Tyr Ser Met Val Gly Asn Trp Ala Lys
                20                  25                  30

GTC CTG ATT GTG GCG CTA CTC TTC GCC GGC GTT GAC GGG GAG ACC TAC     142
Val Leu Ile Val Ala Leu Leu Phe Ala Gly Val Asp Gly Glu Thr Tyr
            35                  40                  45

ACG TCG GGG GGG GCG GCC AGC CAC ACC ACC TCC ACG CTC GCG TCC CTC     190
Thr Ser Gly Gly Ala Ala Ser His Thr Thr Ser Thr Leu Ala Ser Leu
        50                  55                  60

TTC TCA CCT GGG GCG TCT CAG AGA ATC CAG CTT GTG AAT ACC AAC GGC     238
Phe Ser Pro Gly Ala Ser Gln Arg Ile Gln Leu Val Asn Thr Asn Gly
    65                  70                  75

AGC TGG CAC ATC AAC AGG ACT GCC CTA AAC TGC AAT GAC TCC CTC CAC     286
Ser Trp His Ile Asn Arg Thr Ala Leu Asn Cys Asn Asp Ser Leu His
80                  85                  90                  95

ACT GGG TTC CTT GCC GCG CTG TTC TAC ACA CAC AGG TTC AAC TCG TCC     334
Thr Gly Phe Leu Ala Ala Leu Phe Tyr Thr His Arg Phe Asn Ser Ser
                100                 105                 110

GGG TGC CCG GAG CGC ATG GCC AGC TGC CGC CCC ATT GAC TGG TTC GCC     382
Gly Cys Pro Glu Arg Met Ala Ser Cys Arg Pro Ile Asp Trp Phe Ala
            115                 120                 125

CAG GGA TGG GGC CCC ATC ACC TAT ACT GAG CCT GAC AGC CCG GAT CAG     430
Gln Gly Trp Gly Pro Ile Thr Tyr Thr Glu Pro Asp Ser Pro Asp Gln
        130                 135                 140

AGG CCT TAT TGC TGG CAT TAC GCG CCT CGA CCG TGT GGT ATC GTA CCC     478
Arg Pro Tyr Cys Trp His Tyr Ala Pro Arg Pro Cys Gly Ile Val Pro
    145                 150                 155

GCG TCG CAG GTG TGT GGT CCA GTG TAT TGC TTC ACC CCA AGC CCT         523
Ala Ser Gln Val Cys Gly Pro Val Tyr Cys Phe Thr Pro Ser Pro
160                 165                 170
```

( 2 ) INFORMATION FOR SEQ ID NO:21:

( i ) SEQUENCE CHARACTERISTICS:
( A ) LENGTH: 174 amino acids
( B ) TYPE: amino acid
( D ) TOPOLOGY: linear ( i i ) MOLECULE TYPE: protein ( x i ) SEQUENCE DESCRIPTION: SEQ ID NO:21:

```
Ile Pro Gln Ala Val Val Asp Met Val Ala Gly Ala His Trp Gly Val
 1               5                  10                  15

Leu Ala Gly Leu Ala Tyr Tyr Ser Met Val Gly Asn Trp Ala Lys Val
            20                  25                  30

Leu Ile Val Ala Leu Leu Phe Ala Gly Val Asp Gly Glu Thr Tyr Thr
        35                  40                  45

Ser Gly Gly Ala Ala Ser His Thr Thr Ser Thr Leu Ala Ser Leu Phe
```

```
        50                     55                     60

Ser Pro Gly Ala Ser Gln Arg Ile Gln Leu Val Asn Thr Asn Gly Ser
 65                     70                     75                 80

Trp His Ile Asn Arg Thr Ala Leu Asn Cys Asn Asp Ser Leu His Thr
                 85                     90                     95

Gly Phe Leu Ala Ala Leu Phe Tyr Thr His Arg Phe Asn Ser Ser Gly
            100                    105                    110

Cys Pro Glu Arg Met Ala Ser Cys Arg Pro Ile Asp Trp Phe Ala Gln
        115                    120                    125

Gly Trp Gly Pro Ile Thr Tyr Thr Glu Pro Asp Ser Pro Asp Gln Arg
    130                    135                    140

Pro Tyr Cys Trp His Tyr Ala Pro Arg Pro Cys Gly Ile Val Pro Ala
145                    150                    155                    160

Ser Gln Val Cys Gly Pro Val Tyr Cys Phe Thr Pro Ser Pro
                165                    170
```

( 2 ) INFORMATION FOR SEQ ID NO:22:

( i ) SEQUENCE CHARACTERISTICS:
( A ) LENGTH: 402 amino acids
( B ) TYPE: amino acid
( D ) TOPOLOGY: unknown ( i i ) MOLECULE TYPE: protein ( v i ) ORIGINAL SOURCE:
( A ) ORGANISM: Hepatitis C virus ( x i ) SEQUENCE DESCRIPTION: SEQ ID NO:22:

```
Ile Pro Gln Ala Xaa Xaa Asp Met Xaa Ala Gly Ala His Trp Gly Val
1               5                   10                  15

Leu Ala Gly Xaa Ala Tyr Xaa Ser Met Xaa Gly Asn Trp Ala Lys Val
            20                  25                  30

Leu Xaa Val Xaa Leu Leu Phe Ala Gly Val Asp Xaa Xaa Thr Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Gly Xaa Xaa Xaa Xaa Xaa Gln Leu Xaa Xaa Thr Asn Gly Ser
65                  70                  75                  80

Trp His Xaa Asn Xaa Thr Ala Leu Asn Cys Asn Xaa Ser Leu Xaa Xaa
                85                  90                  95

Gly Xaa Xaa Ala Xaa Leu Xaa Tyr Xaa His Xaa Phe Xaa Xaa Ser Xaa
            100                 105                 110

Xaa Xaa Xaa Xaa Xaa Ala Xaa Cys Xaa Xaa Xaa Xaa Xaa Phe Xaa Gln
        115                 120                 125

Gly Trp Xaa Pro Ile Xaa Xaa Xaa Xaa Xaa Xaa Xaa Xaa Xaa Xaa Xaa
    130                 135                 140

Pro Tyr Cys Trp His Tyr Xaa Pro Xaa Xaa Cys Xaa Xaa Val Pro Ala
145                 150                 155                 160

Xaa Xaa Val Cys Gly Pro Val Tyr Cys Phe Thr Pro Ser Pro Val Val
                165                 170                 175

Val Gly Thr Thr Asp Arg Xaa Gly Xaa Pro Thr Tyr Xaa Trp Gly Xaa
            180                 185                 190

Asn Xaa Thr Asp Val Xaa Xaa Leu Xaa Asn Thr Arg Pro Pro Xaa Gly
        195                 200                 205

Asn Trp Phe Gly Cys Thr Trp Met Asn Xaa Thr Gly Phe Thr Lys Xaa
    210                 215                 220
```

-continued

Cys Gly Xaa Pro Pro Cys Xaa Ile Xaa Gly Xaa Gly Asn Asn Thr Leu
225 230 235 240

Xaa Cys Pro Thr Asp Cys Phe Arg Lys His Pro Xaa Ala Thr Tyr Xaa
245 250 255

Xaa Cys Gly Ser Gly Pro Trp Xaa Thr Pro Arg Cys Xaa Val Xaa Tyr
260 265 270

Pro Tyr Arg Leu Trp His Tyr Pro Cys Thr Xaa Asn Xaa Thr Xaa Phe
275 280 285

Lys Xaa Arg Met Tyr Val Gly Gly Xaa Glu His Arg Leu Xaa Ala Ala
290 295 300

Cys Asn Trp Thr Arg Gly Xaa Arg Cys Xaa Leu Glu Asp Arg Asp Arg
305 310 315 320

Xaa Glu Leu Ser Pro Leu Leu Leu Xaa Thr Thr Xaa Trp Gln Xaa Leu
325 330 335

Pro Cys Ser Phe Thr Thr Leu Pro Ala Leu Ser Thr Gly Leu Ile His
340 345 350

Leu His Xaa Asn Xaa Val Asp Val Gln Tyr Leu Tyr Gly Xaa Gly Ser
355 360 365

Xaa Xaa Xaa Ser Xaa Xaa Ile Xaa Trp Glu Tyr Xaa Xaa Leu Leu Phe
370 375 380

Leu Leu Leu Ala Asp Ala Arg Val Cys Xaa Cys Leu Trp Met Met Leu
385 390 395 400

Leu Ile ( 2 ) INFORMATION FOR SEQ ID NO:23:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:23:

GCTATCAGCA GCATCATCCA 20

( 2 ) INFORMATION FOR SEQ ID NO:24:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:24:

CAGNTANTCC GGATCCCNCA AG 22

( 2 ) INFORMATION FOR SEQ ID NO:25:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:25:

GTAAAACGAC GGCCAGT 17

( 2 ) INFORMATION FOR SEQ ID NO:26:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:26:

CAGGAAACAG CTATGAC 17

( 2 ) INFORMATION FOR SEQ ID NO:27:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:27:

GGACTAGTCC 10

( 2 ) INFORMATION FOR SEQ ID NO:28:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:28:

CTAGAGAATT CGGTAC 16